United States Patent
Ji et al.

(10) Patent No.: US 12,144,600 B2
(45) Date of Patent: Nov. 19, 2024

(54) BIOIMPEDANCE MEASUREMENT DEVICE AND OPERATION METHOD THEREOF

(71) Applicant: INBODY CO., LTD., Seoul (KR)

(72) Inventors: Chang Su Ji, Yongin-si (KR); Ki Chul Cha, Seoul (KR)

(73) Assignee: INBODY CO., LTD., Seoul (KR)

( * ) Notice: Subject to any disclaimer, the term of this patent is extended or adjusted under 35 U.S.C. 154(b) by 686 days.

(21) Appl. No.: 17/426,459

(22) PCT Filed: Jan. 15, 2020

(86) PCT No.: PCT/KR2020/000739
§ 371 (c)(1),
(2) Date: Jul. 28, 2021

(87) PCT Pub. No.: WO2020/159118
PCT Pub. Date: Aug. 6, 2020

(65) Prior Publication Data
US 2022/0095946 A1   Mar. 31, 2022

(30) Foreign Application Priority Data

Jan. 29, 2019  (KR) .................. 10-2019-0011295
Feb. 26, 2019  (WO) ................ PCT/KR2019/002320
(Continued)

(51) Int. Cl.
*A61B 5/0537*  (2021.01)
*A61B 5/00*    (2006.01)
*A61B 5/25*    (2021.01)

(52) U.S. Cl.
CPC .............. *A61B 5/0537* (2013.01); *A61B 5/25* (2021.01); *A61B 5/742* (2013.01); *A61B 2562/0247* (2013.01)

(58) Field of Classification Search
CPC . A61B 5/25; A61B 2562/0247; A61B 5/0537; A61B 5/742; A61B 5/7271; A61B 5/7221
See application file for complete search history.

(56) References Cited

U.S. PATENT DOCUMENTS

| 10,154,460 | B1 * | 12/2018 | Miller ..................... A61B 5/742 |
| 11,642,038 | B1 * | 5/2023 | Moyer ................ A61B 5/6843 600/547 |

(Continued)

FOREIGN PATENT DOCUMENTS

| CN | 201675940 U | * 12/2010 | ........... A61B 5/0537 |
| JP | 2007301093 A |   11/2007 | |

(Continued)

OTHER PUBLICATIONS

Translated Chinese First Office Action, App. No. 202080022943.8, dated Dec. 26, 2023, pp. 1-16.

(Continued)

*Primary Examiner* — Devin B Henson
(74) *Attorney, Agent, or Firm* — BOND, SCHOENECK & KING, PLLC; George R. McGuire

(57) ABSTRACT

A bioimpedance measurement device and an operation method thereof are disclosed. The disclosed bioimpedance measurement device comprises: a body part which accommodates a measurement circuit and comprises a grip that can be gripped by a hand; a first electrode and a second electrode which are coupled to a first shaft provided on one side of the body part and rotate about the first shaft; and a third electrode and a fourth electrode which are coupled to a second shaft provided on the one side of the body part at a position different from that of the first shaft. When a subject to be measured is surrounded by and comes into contact with (Continued)

the first electrode, the second electrode, the third electrode, and the fourth electrode, the bioimpedance of the subject to be measured is measured.

19 Claims, 32 Drawing Sheets

(30) Foreign Application Priority Data

May 17, 2019 (KR) .................. 10-2019-0057959
Aug. 8, 2019 (KR) .................. 10-2019-0096704

(56) References Cited

U.S. PATENT DOCUMENTS

| 2008/0243026 | A1* | 10/2008 | Tsuji | A61B 5/0537 |
| | | | | 600/547 |
| 2008/0306401 | A1* | 12/2008 | Okura | A61B 5/0537 |
| | | | | 600/547 |
| 2013/0096456 | A1* | 4/2013 | Fukuda | A61B 5/0537 |
| | | | | 600/547 |
| 2013/0102870 | A1 | 4/2013 | Murakawa et al. | |

FOREIGN PATENT DOCUMENTS

| JP | 2008302106 | A | | 12/2008 | |
| JP | 2009050412 | A | | 3/2009 | |
| KR | 100423678 | B | | 3/2004 | |
| KR | 1020160065330 | A | | 6/2016 | |
| KR | 20180097833 | A | * | 2/2017 | .......... A61B 5/4869 |
| KR | 1020180077897 | A | | 7/2018 | |
| KR | 1020180087043 | A | | 8/2018 | |
| KR | 20200069402 | A | * | 12/2018 | .......... A61B 5/4869 |
| WO | 2007129521 | A1 | | 11/2007 | |
| WO | 2018025829 | A1 | | 2/2018 | |

OTHER PUBLICATIONS

International Search Report and Written Opinion Form PCT/ISA/210 and PCT/ISA/237, International Application No. PCT/KR2020/000739, pp. 1-8 International Filing Date Jan. 15, 2020, mailing date of search report Apr. 13, 2020.

* cited by examiner

BIOIMPEDANCE MEASUREMENT DEVICE AND OPERATION METHOD THEREOF

CROSS REFERENCE TO RELATED APPLICATIONS

This is a National Stage Application filed under 35 U.S.C. 371 based on International Patent Application No. PCT/KR2020/000739, filed on Jan. 15, 2020, which claims priority to Korean Patent Application 10-2019-0011295 filed Jan. 29, 2019; International Patent Application PCT/KR2019/002320, filed Feb. 26, 2019; Korean Patent Application 10-2019-0057959 filed May 17, 2019; and Korean Patent Application 10-2019-0096704 filed Aug. 8, 2019. The entire disclosures of each of the foregoing are hereby incorporated herein by reference in their entireties.

TECHNICAL FIELD

The following description relates to a bioimpedance measurement device and an operation method thereof.

BACKGROUND ART

A device for measuring a body composition using different electrical resistances such as fat and muscle is conventionally known. The device for measuring a body composition may measure a bioimpedance by bring an electrode into contact with to a measurement part, and accordingly may determine the body composition. In order to accurately calculate the body composition, not only the bioimpedance but also shape information of the measurement part is required. Therefore, it is important to accurately identify a shape of the measurement part in addition to accuracy in bioimpedance measurement. In addition, a capability to measure an impedance and a circumference of a measurement part in a simple manner, a capability to measure a body composition as a single device without an additional auxiliary device, and the like are important in terms of improvement in ease of a user.

DISCLOSURE OF THE INVENTION

Technical Goals

An aspect provides a bioimpedance measurement device that is easy in terms of use because it can be gripped by one hand, and that is capable of measuring a bioimpedance with one device without a need for an additional device, further increasing accuracy in body shape identification, and increasing precision and accuracy in body composition measurement by maintaining a constant degree of contact and pressure of an electrode regardless of a shape of a measurement part.

Another aspect provides a bioimpedance measurement device that is capable of measuring an impedance of any desired part without limiting an impedance measurable part to a specific part such as an abdomen or the like.

Still another aspect provides bioimpedance measurement and measurement of a length and a circumference of a measurement part that may be performed with one device, and thus an additional device is not required, thereby improving ease of use and portability.

Technical Solutions

According to an aspect, there is provided a bioimpedance measurement device including a body part configured to accommodate a measurement circuit, the body part including a grip that can be gripped by a hand, a first electrode and a second electrode coupled to a first shaft provided on one side of the body part, the first electrode and the second electrode configured to rotate about the first shaft, and a third electrode and a fourth electrode coupled to a second shaft provided on the one side of the body part at a position different from that of the first shaft, the third electrode and the fourth electrode configured to rotate about the second shaft. The bioimpedance measurement device may be configured to measure a bioimpedance of a subject to be measured when the subject to be measured approaches, and is surrounded by and comes into contact with the first electrode, the second electrode, the third electrode, and the fourth electrode.

In the bioimpedance measurement device according to an aspect, the second electrode may be configured to accommodate the subject to be measured deeper than when the subject to be measured begins to come into contact with the second electrode, by being pressed by the subject to be measured and rotating toward the grip.

In the bioimpedance measurement device according to an aspect, the second electrode may be supported by an elastic body so as to be restored back to a position before rotation when the subject to be measured is spaced apart.

In the bioimpedance measurement device according to an aspect, the fourth electrode may be adjacent to the second electrode, and may configured to accommodate the subject to be measured deeper than when the subject to be measured begins to come into contact with the fourth electrode, by being pressed by the subject to be measured and rotating toward the grip.

In the bioimpedance measurement device according to an aspect, a degree to which the fourth electrode rotates toward the grip may be different from a degree to which the second electrode rotates toward the grip.

In the bioimpedance measurement device according to an aspect, the measurement circuit may be configured to estimate a part of the subject to be measured that is in contact by comparing a degree to which the second electrode rotates toward the grip and a degree to which the fourth electrode rotates toward the grip, while being pressed by the subject to be measured.

In the bioimpedance measurement device according to an aspect, the measurement circuit may be configured to estimate a part of the subject to be measured that is in contact by comparing a degree to which the first electrode is spread and a degree to which the third electrode is spread, while being pressed by the subject to be measured.

In the bioimpedance measurement device according to an aspect, the measurement circuit may be configured to determine that the bioimpedance measurement result is not valid when at least one of the second electrode and the fourth electrode rotates to a limit toward the grip and is pressed, while being pressed by the subject to be measured.

In the bioimpedance measurement device according to an aspect, the first electrode and the third electrode may be spread or gathered depending on a circumference of the subject to be measured that approaches and comes into contact.

In the bioimpedance measurement device according to an aspect, the measurement circuit may be configured to estimate a circumference of the subject to be measured using at least one of a degree to which the second electrode rotates toward the grip, a degree to which the fourth electrode rotates toward the grip, a degree to which the first electrode is spread or gathered, and a degree to which the third electrode is spread or gathered, while the subject to be measured approaches and comes into contact.

The bioimpedance measurement device according to an aspect may further include a pressure sensor configured to measure a pressure when the subject to be measured approaches, and is surrounded by and comes into contact with the first electrode, the second electrode, the third electrode, and the fourth electrode. The bioimpedance of the subject to be measured may be measured when the pressure measured by the pressure sensor falls within a predetermined range.

In the bioimpedance measurement device according to an aspect, the body part may include a first part including the first to fourth electrodes and a second part including the grip that can be gripped by the hand, and the pressure sensor may be disposed between the first part and the second part, and may be configured to measure a pressure applied by the first part to the second part when the subject to be measured approaches, and is surrounded by and comes into close contact with the first electrode, the second electrode, the third electrode, and the fourth electrode.

The bioimpedance measurement device according to an aspect may further include a communicator configured to transmit, to an external device, the bioimpedance and a circumference of the subject to be measured. A body composition of the subject to be measured may be determined based on at least one of the bioimpedance and the circumference of the subject to be measured, a weight and a whole-body impedance or body part-specific impedance of the subject to be measured that are measured by the external device, and body information of the subject to be measured that is inputted into the external device.

The bioimpedance measurement device according to an aspect may further include a communicator configured to transmit, to a server, the bioimpedance and a circumference of the subject to be measured. A body composition of the subject to be measured may be determined based on at least one of the bioimpedance and the circumference of the subject to be measured, a weight and a whole-body impedance or body part-specific impedance of the subject to be measured that are measured by an external device that performs communication with the bioimpedance measurement device, body information of the subject to be measured that is inputted into the external device, and biometric data stored in the server.

According to another aspect, there is provided an operation method of a bioimpedance measurement device including sensing a movement of at least one of a first electrode, a second electrode, a third electrode, and a fourth electrode provided in the bioimpedance measurement device when a subject to be measured approaches the bioimpedance measurement device, and is surrounded by and comes into contact with the bioimpedance measurement device, and measuring a bioimpedance of the subject to be measured using at least one of the first electrode, the second electrode, the third electrode, and the fourth electrode. The first electrode and the second electrode may be coupled to a first shaft provided on one side of the bioimpedance measurement device to rotate about the first shaft, and the third electrode and the fourth electrode may be coupled to a second shaft on the one side of the bioimpedance measurement device at a position different from that of the first shaft to rotate about the second shaft.

In the operation method of the bioimpedance measurement device according to another aspect, the sensing of the movement may include estimating a circumference of the subject to be measured using at least one of a degree to which the second electrode rotates toward the grip, a degree to which the fourth electrode rotates toward the grip, a degree to which the first electrode is spread or gathered, and a degree to which the third electrode is spread or gathered, while the subject to be measured approaches and comes into contact.

According to still another aspect, there is provided a bioimpedance measurement device including a body part configured to accommodate a measurement circuit, the body part including a grip that can be gripped by a hand, a first electrode coupled to a first shaft provided on one side of the body part, the first electrode configured to rotate about the first shaft, a third electrode coupled to a second shaft provided on the one side of the body part at a position different from that of the first shaft, the third electrode configured to rotate about the second shaft, a second electrode positioned adjacent to the first electrode between the first electrode and the third electrode, and a fourth electrode positioned adjacent to the third electrode between the first electrode and the third electrode. The bioimpedance measurement device may be configured to measure a bioimpedance of a subject to be measured when the subject to be measured approaches, and is surrounded by and comes into contact with the first electrode, the second electrode, the third electrode, and the fourth electrode.

In the bioimpedance measurement device according to still another aspect, the first electrode and the third electrode may be spread in different directions to come into close contact with the subject to be measured as the subject to be measured approaches and comes into contact.

In the bioimpedance measurement device according to still another aspect, the first electrode and the third electrode may be coupled to the one side of the body part, and may be respectively disposed on a plurality of segment members that are rotatably coupled to each other. The first to fourth electrodes may form a sample part including at least two electrodes for applying a current and at least two electrodes for measuring a voltage. An angle between respective segment members may be adjusted so that one or more electrodes disposed on the plurality of segment members come into contact with the subject to be measured to correspond to a shape or thickness of the subject to be measured.

The bioimpedance measurement device according to still another aspect may further include an adjustment mechanism disposed on the gripping surface, the adjustment mechanism configured to adjust rotation of one or more segment members of the sample part. The sample part may be connected to the adjustment mechanism so that an angle between the plurality of segment members is changed by operation of the adjustment mechanism. When an operation state of the adjustment mechanism is released after at least some of the plurality of electrodes are brought into contact with a measurement part of the subject to be measured, the angle between the respective segment members may be adjusted so that the electrodes disposed on the plurality of segment members come into contact with the subject to be measured to correspond to the shape or thickness of the subject to be measured.

The bioimpedance measurement device according to still another aspect may further include a length measurement part coupled to another side of the body part, the length measurement part configured to measure a circumference or length of the subject to be measured, and the length measurement part may be configured to rotate about a rotational shaft penetrating through the other side of the body part, and measure the circumference or length of the subject to be measured based on the number of rotations measured by performing a rolling operation on a surface of the subject to be measured.

In the bioimpedance measurement device according to still another aspect, detent feedback may be provided when the length measurement part rotates in close contact with the subject to be measured so as to measure the circumference or length of the subject to be measured.

In the bioimpedance measurement device according to still another aspect, feedback may be provided based on at least one of a rotational speed and a rotational direction of the length measurement part when the length measurement part rotates in close contact with the subject to be measured so as to measure the circumference or length of the subject to be measured.

In the bioimpedance measurement device according to still another aspect, the sample part and the length measurement part may be integrally formed with the body part. The circumference or length of the subject to be measured may be measured by the length measurement part coupled to the other side of the body part. An impedance of the subject to be measured may be measured by the sample part coupled to the one side of the body part.

The bioimpedance measurement device according to still another aspect may further include an angle sensor configured to measure a degree to which each of the first electrode and the third electrode rotates. A circumference or length of the subject to be measured may be determined based on an output of the angle sensor.

The bioimpedance measurement device according to still another aspect may further include a pressure sensor that comes into close contact with the subject to be measured, the pressure sensor configured to measure a pressure applied to one or more electrodes of the first to fourth electrodes.

In the bioimpedance measurement device according to still another aspect, feedback depending on whether the pressure applied to the one or more electrodes of the first to fourth electrodes by close contact of the subject to be measured satisfies a predetermined condition may be determined and provided based on an output of the pressure sensor.

In the bioimpedance measurement device according to still another aspect, the feedback may include at least one of a visual screen and an audible sound effect.

In the bioimpedance measurement device according to still another aspect, feedback instructing an operation of measuring the bioimpedance may be provided when there is no pressure applied to the one or more electrodes of the first to fourth electrodes because the subject to be measured does not yet come into close contact.

In the bioimpedance measurement device according to still another aspect, measurement of the bioimpedance may be completed when a change amount of the measured bioimpedance and an output of the pressure sensor satisfy a predetermined condition for a first predetermined time.

In the bioimpedance measurement device according to still another aspect, feedback instructing re-measurement of the bioimpedance may be provided when the predetermined condition is not satisfied within a second predetermined time.

The bioimpedance measurement device according to still another aspect may further include a pressure display part disposed on the one side of the body part, the pressure display part configured to display a pressure value measured by the pressure sensor.

The bioimpedance measurement device according to still another aspect may further include at least one angle adjustment part disposed on the body part, the angle adjustment part configured to adjust a rotational angle of a segment member of the sample part.

In the bioimpedance measurement device according to still another aspect, the angle adjustment part may include an adjustment mechanism configured to rotate about a rotational shaft penetrating through the one side of the body part, the adjustment mechanism having one side exposed to an outside of the body part, a linear motion member coupled to another side of the adjustment mechanism, the linear motion member having coupling grooves formed at opposite longitudinal ends thereof, and a protrusion formed on one side may be coupled to the coupling groove in a manner capable of performing a linear motion, and another side may be connected to the segment member.

In the bioimpedance measurement device according to still another aspect, health information of the subject to be measured may be calculated by synthesizing information received from the sample part and a length measurement part.

The bioimpedance measurement device according to still another aspect may further include a communicator configured to transmit, to an external device, the bioimpedance and a circumference of the subject to be measured. A body composition of the subject to be measured may be determined based on at least one of the bioimpedance and the circumference of the subject to be measured, a weight and a whole-body impedance or body part-specific impedance of the subject to be measured that are measured by the external device, and body information of the subject to be measured that is inputted into the external device.

The bioimpedance measurement device according to still another aspect may further include a communicator configured to transmit, to a server, the bioimpedance and a circumference of the subject to be measured. A body composition of the subject to be measured may be determined based on at least one of the bioimpedance and the circumference of the subject to be measured, a weight and a whole-body impedance or body part-specific impedance of the subject to be measured that are measured by an external device that performs communication with the bioimpedance measurement device, body information of the subject to be measured that is inputted into the external device, and biometric data stored in the server.

EFFECTS

According to an aspect, a constant degree of pressing a subject to be measured may be maintained because an electrode comes into contact with the subject to be measured regardless of a shape of a measurement part or a body shape, thereby improving precision and accuracy in measuring a bioimpedance of the subject to be measured.

According to an aspect, a bioimpedance and a circumference of a measurement part may be measured by gripping a bioimpedance measurement device with one hand, thereby improving ease of use.

According to an aspect, a structure in which a second electrode and a fourth electrode provided in a bioimpedance measurement device are pressed by a subject to be measured and rotate toward a grip may make it possible to effectively measure not only a bioimpedance of a large-sized subject to be measured but also a bioimpedance of a small-sized subject to be measured.

According to an aspect, a circumference of a subject to be measured may be determined based on a degree of movements of a plurality of electrodes when the subject to be measured approaches, and is surrounded by and comes into contact with the plurality of electrodes, thereby performing bioimpedance measurement and circumference measurement at once without additional equipment or operation.

According to an aspect, whether a subject to be measured comes into contact with a bioimpedance measurement device excessively, weakly, or appropriately may be identified depending on a degree to which a second electrode and a fourth electrode provided in the bioimpedance measurement device are pressed by the subject to be measured and rotate toward a grip, thereby improving accuracy in measurement by guiding an appropriate contact pressure.

BEST MODE FOR CARRYING OUT THE INVENTION

Figure 1A:
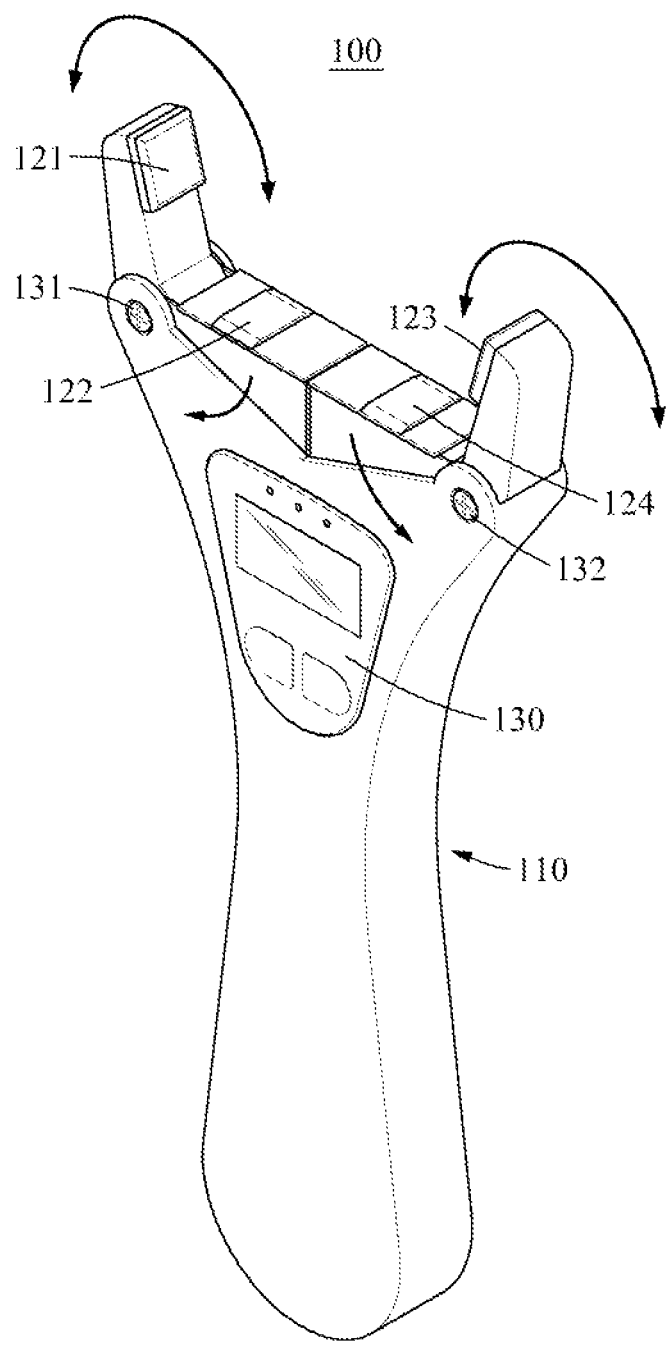
FIGS. 1A and 1B are diagrams illustrating a bioimpedance measurement device according to an example embodiment.

Specific structural or functional descriptions of example embodiments are set forth for purpose of illustration only, and may be changed and implemented in various forms. Accordingly, example embodiments are not limited to a specific form disclosed, and the present specification covers changes, equivalents, or substitutes falling in the technical spirit.

Terms such as first, second, and the like may be used herein to describe components. These terms not used merely to distinguish a corresponding component from another component. For example, a first component may be referred to a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component.

As used herein, the singular forms "a," "an," and "the," are intended to include the plural forms as well, unless the context clearly indicates otherwise. It will be further understood. that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

Unless otherwise defined, all terms, including technical and scientific terms, used herein have the same meaning as commonly understood by one skilled in the art to which the example embodiments pertain. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, example embodiments will be described in detail with reference to the accompanying drawings. The specific structural or functional descriptions below are merely exemplified for the purpose of describing the example embodiments, and example embodiments should not be construed as being limited to the example embodiments set forth herein. Various modifications and variations may be made from the descriptions by those skilled in the art. In addition, the same reference numerals in each drawing indicate the same members, and well-known functions and structures will be omitted.

Figure 1B:
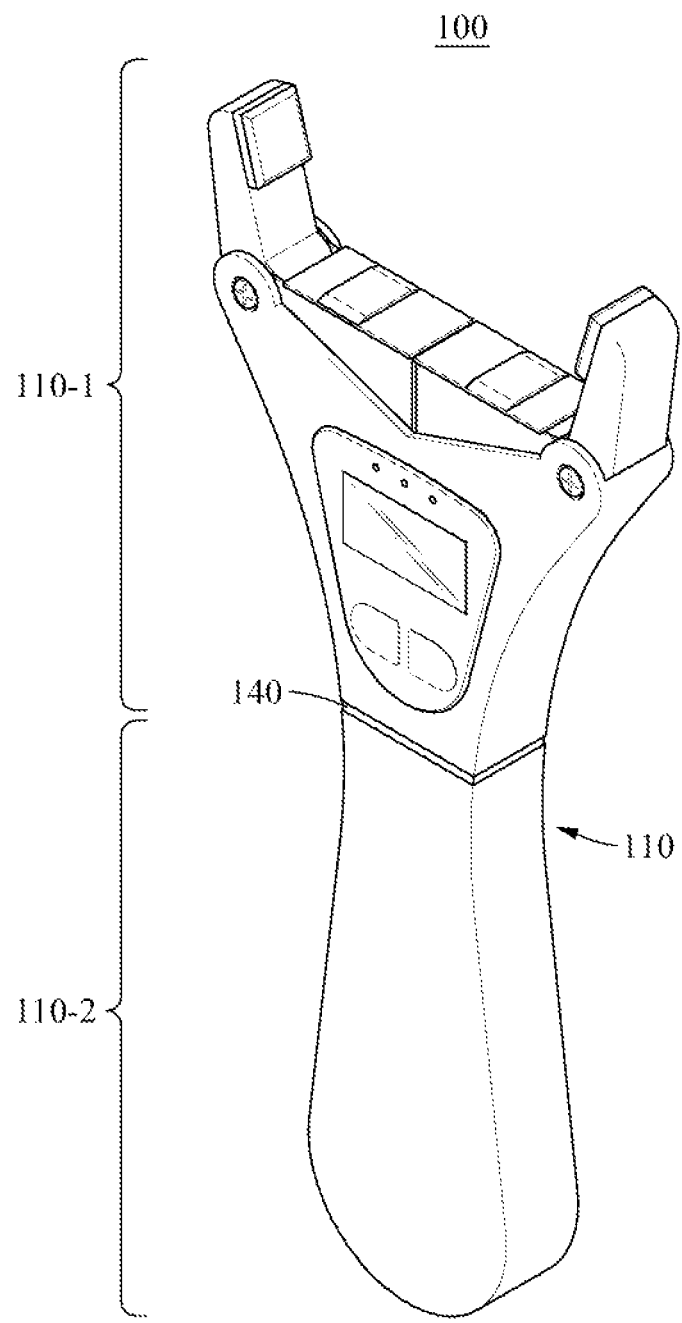

FIGS. 1A and 1B are diagrams illustrating a bioimpedance measurement device according to an example embodiment.

Referring to FIG. 1A, a bioimpedance measurement device 100 according to an example embodiment includes a body part 110 and a plurality of electrodes 121 to 124.

The body part 110 may accommodate a measurement circuit and include a grip that can be gripped by a hand. For example, the body part 110 may be gripped by an examinee corresponding to a subject to be measured or an examiner who performs measurement of a bioimpedance of the examinee. The measurement circuit may be connected to the plurality of electrodes 121 to 124 to measure a bioimpedance of the subject to be measured. In addition, the measurement circuit may determine, based on the measured bioimpedance, a body composition (for example, an amount of body fat and the like) of the subject to be measured.

The plurality of electrodes 121 to 124 may include one or more pairs of electrodes for applying a current and one or more pairs of electrodes for applying a voltage. The bioimpedance measurement device 100 may apply a predetermined current using the electrodes for applying a current among the electrodes 121 to 124 that are in contact with the subject to be measured, and may measure a potential difference in a path through which a corresponding current flows using the electrodes for applying a voltage, thereby measuring a bioimpedance of the subject to be measured. For example, the bioimpedance measurement device 100 may apply a high-frequency current generated by a built-in current source from one point to another point of the subject to be measured, and may measure the bioimpedance of the subject to be measured based on measurement of the applied current (current flowing through a body) and a potential difference between two points in a path through which the current flows.

The plurality of electrodes 121 to 124 may rotate about a first shaft 131 or a second shaft 132 for stable contact with the subject to be measured. The first shaft 131 or the second shaft 132 may be provided on one side of the body part 110, and may have different positions from each other. The first shaft 131 and the second shaft 132 may include an elastic body therein. When the subject to be measured approaches and does not come into contact with the elastic body included therein, the first electrode 121 and the third electrode 123 that rotate about the first shaft 131 and the second shaft 132 may be maintained in a state of being retracted at a predetermined angle. A general spring may be used as the elastic body, but is not limited thereto, and any material may be used as long as the first electrode 121 and the third electrode 123 may be maintained in a state of being retracted at a predetermined angle when the subject to be measured approaches and does not come into contact.

The first electrode 121 and the second electrode 122 may rotate about the first shaft 131, and the third electrode 123 and the fourth electrode 124 may rotate about the second shaft 132. Although it will be described in detail below, the first electrode 121 and the third electrode 123 may be spread or gathered depending on a circumference of the subject to be measured when the subject to be measured approaches and comes into contact. For example, when a subject to be measured having a circumference greater than a reference value approaches and comes into contact, the first electrode 121 and the third electrode 123 may be spread. Conversely, when a subject to be measured having a circumference less than the reference value approaches and comes into contact, the first electrode 121 and the third electrode 123 may be gathered.

When the subject to be measured approaches and comes into contact, the second electrode 122 and the fourth electrode 124 may be pressed by the subject to be measured and rotate toward a grip, thereby accommodating the subject to be measured deeper than when the subject to be measured begins to come into contact with the second electrode 122 and the fourth electrode 124. In addition, the second electrode 122 and the fourth electrode 124 may be supported by the elastic body so as to restore a position before rotation when the subject to be measured is spaced apart. At this time, degrees to which the second electrode 122 and the fourth electrode 124 respectively rotate toward the grip may be the same or different from each other depending on a shape of the subject to be measured.

In addition, while the subject to be measured approaches and comes into contact, the measurement circuit may estimate the circumference of the subject to be measured using at least one of a degree to which the second electrode 122 rotates toward the grip, a degree to which the fourth electrode 124 rotates toward the grip, a degree to which the first electrode 121 is spread or gathered, and a degree to which the third electrode 123 is spread or gathered. The bioimpedance measurement device 100 may determine a body composition of the subject to be measured without an additional device based on the measured bioimpedance of the subject to be measured and the estimated circumference of the subject to be measured. However, the bioimpedance measurement device may be linked with another device so as to further increase precision and accuracy in body composition measurement.

At least one of the bioimpedance, body composition, and body composition of the subject to be measured determined by the bioimpedance measurement device 100 may be displayed on a display 130.

In addition, depending on the example embodiment, the bioimpedance measurement device 100 may further include a pressure sensor. For example, at least one of the plurality of electrodes 121 to 124 may include a pressure sensor on one side of a corresponding electrode. However, a position of the pressure sensor is not limited thereto, and any position suitable for measuring a pressure applied to the corresponding electrode by close contact with the examinee is possible without limitation.

For example, the pressure sensor may be included in the second electrode 122 and the fourth electrode 124 positioned at the center. When the second electrode 122 and the fourth electrode 124 come into contact with the examinee, the second electrode 122 and the fourth electrode 124 may be retracted inward, and at this time, it is possible to identify whether the examinee comes into contact with the electrode by the pressure sensor disposed on one side of the second electrode 122 and the fourth electrode 124 being pressed, and whether the electrode presses the examinee with a degree of pressure required to accurately measure an impedance. The second electrode 122 and the fourth electrode 124 may include an elastic material on one side thereof or therein. When the examinee comes into close contact and is pressed by the elastic material, a corresponding electrode may be retracted inward, and a pressure may be transmitted to the pressure sensor disposed on one side of the corresponding electrode, and the pressure may be measured, and when the examinee is detached from the electrode after pressure measurement and impedance measurement are completed, the pressure sensor may be restored to an initial state before being pressed. In addition, the pressure sensor may be positioned in various parts, which will be described later with reference to FIG. 2B.

A pressure measured by the pressure sensor may be provided to the examinee. For example, the measured pressure may be displayed on the display 130. Alternatively, the measured pressure may be displayed through a pressure gauge or LED lamp. When an appropriate pressure for impedance measurement is not applied, a message informing the examinee that contact is not properly made may be also displayed. For example, when a measurement value of the pressure sensor is less than a first predetermined threshold pressure, a message indicating that a greater intensity of pressure needs to be applied may be provided to the examinee. Alternatively, when the measurement value of the pressure sensor is greater than a second predetermined threshold pressure, a message indicating that a less intensity of pressure needs to be applied may be provided to the examinee.

The bioimpedance measurement device 100 may be configured to automatically measure an impedance of the examinee when it is determined that an appropriate level of pressure is applied based on the measurement value of the pressure sensor. For example, the bioimpedance measurement device 100 may determine that the appropriate level of pressure is applied when the measurement value of the pressure sensor is greater than or equal to a predetermined threshold pressure. Alternatively, the bioimpedance measurement device 100 may determine that the appropriate level of pressure is applied when the measurement value of the pressure sensor falls within a predetermined threshold range.

Referring to FIG. 1B, the bioimpedance measurement device 100 according to an example embodiment may include a first part 110-1 and a second part 110-2. The first part 110-1, which is a part including first to fourth electrodes, may be a part that is in close contact with the subject to be measured. The second part 110-2 may be a part including a grip that can be gripped by a hand.

The pressure sensor 140 according to an example embodiment may be disposed between the first part 110-1 and the second part 110-2 of the bioimpedance measurement device 100. When the subject to be measured approaches the bioimpedance measurement device 100 and is surrounded by and comes into close contact with the first to fourth electrodes, a pressure applied from the first part 110-1 to the second part 110-2 may be generated, and the pressure sensor 140 may measure the generated pressure. Through this structure that is quantitatively less affected by eccentricity and the like, the pressure may be measured with high accuracy even when the subject to be measured does not exactly come into close contact with the bioimpedance measurement device 100.

For ease of description, four electrodes are illustrated in FIGS. 1A and 1B, but in addition, various numbers of electrodes may be applied to the bioimpedance measurement device 100 without limitation.

Figure 2:
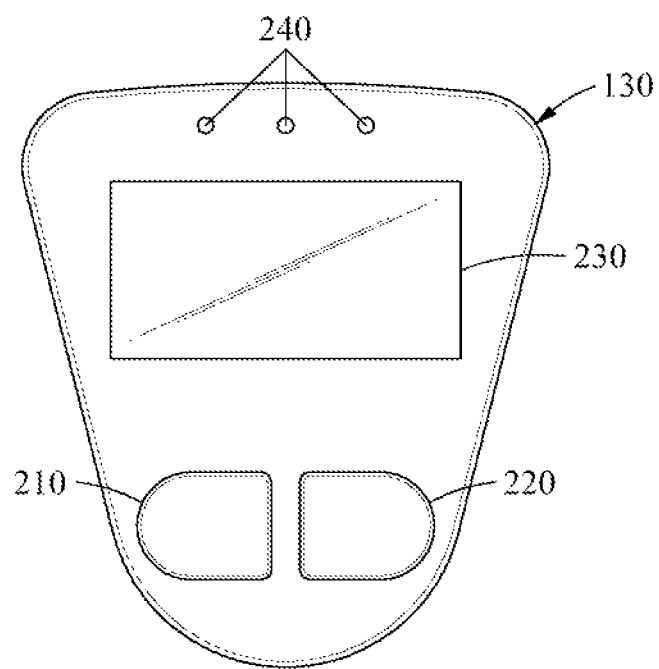
FIGS. 2 and 3 are diagrams illustrating a body part of a bioimpedance measurement device according to an example embodiment.
Figure 3:
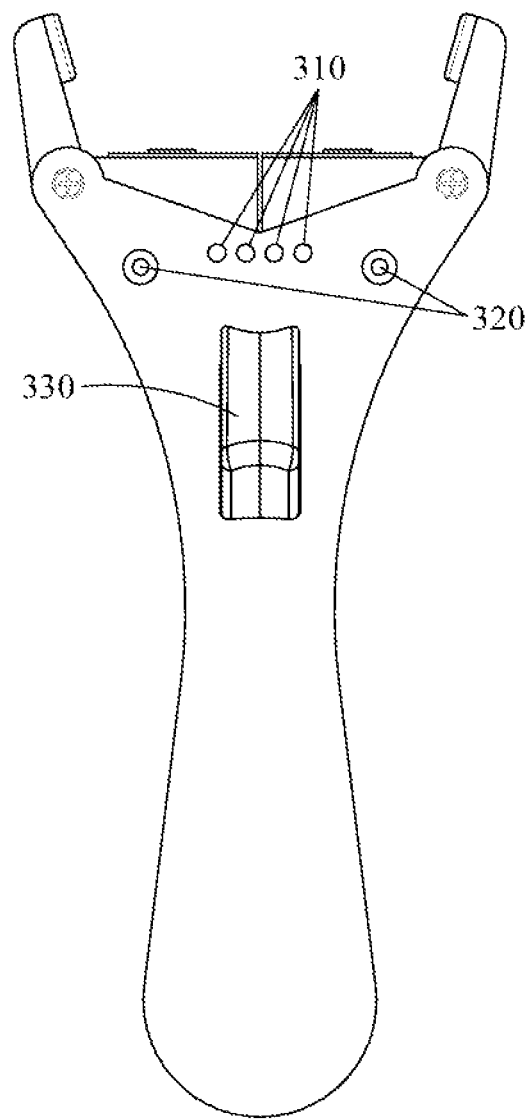

FIGS. 2 and 3 are diagrams illustrating a body part of a bioimpedance measurement device according to an example embodiment.

Referring to FIG. 2, a display part 130 according to an example embodiment may include a first button 210, a second button 220, a liquid crystal part 230, and an LED lamp 240.

The first button 210 may be a zero-point button that initializes existing measurement data. By clicking the first button 210 before performing a new measurement, existing data may be initialized.

The second button 220 may be a mode conversion button capable of performing mode conversion between a plurality of modes including a first mode for measuring a bioimpedance of a subject to be measured and a second mode for measuring a circumference or length of the subject to be measured. However, depending on the example embodiment, when the subject to be measured approaches and comes into contact with a plurality of electrodes, the bioimpedance and the circumference of the subject to be measured may be determined at once without mode conversion, and in this case, a mode conversion function may not be used.

Functions of the first button 210 and the second button 220 are not limited to the above-described example embodiment, and in addition, may be used without limitation as buttons for executing various functions required by the bioimpedance measurement device.

The liquid crystal part 230 may display whether the subject to be measured properly comes into contact with the plurality of electrodes, and a bioimpedance, circumference, body composition, body composition and the like of the subject to be measured. In addition, various information that may be displayed by the bioimpedance measurement device may be displayed on the liquid crystal part 230 without limitation.

The LED lamp 240 may display information about a state in which at least one of the bioimpedance and circumference of the subject to be measured is measured. For example, whether the plurality of electrodes come into contact with the subject to be measured while applying a proper pressure to the subject to be measured may be displayed on the LED lamp 240. In addition, various pieces of information may be displayed on the LED lamp 240 without limitation.

Referring to FIG. 3, a charging/communication terminal 310, a magnetic material 320, and an adjustment mechanism 330 may be provided on a rear surface of a body part according to an example embodiment. The charging/communication terminal 310 may electrically connect an external power source and a bioimpedance measurement device to each other when the bioimpedance measurement device is charged, and may connect communication between an external device and the bioimpedance measurement device when communication with the external device is performed. The magnetic material 320 may be for preventing the bioimpedance measurement device from being easily separated when the bioimpedance measurement device is mounted on an additional charger. The adjustment mechanism 330 may be coupled to an inner surface of a lower cover of the body part, and may be rotatably coupled to the inner surface about a specific rotational shaft. The adjustment mechanism 330 may penetrate through the lower cover of the body part and protrude from an outer surface of the lower cover. When the adjustment mechanism 330 is pressed or a pressure applied to the adjustment mechanism 330 is released, the adjustment mechanism 330 may rotate about the rotational shaft. When the adjustment mechanism 330 is pressed, the first electrode 121 and the third electrode 123 of FIG. 1 may be spread in opposite directions, and in this state, when the pressure applied to the adjustment mechanism 330 is released after the bioimpedance measurement device comes into close contact with subject to be measured, the electrodes of the bioimpedance measurement device may naturally come into contact with the subject to be measured with an appropriate pressure.

Figure 4:
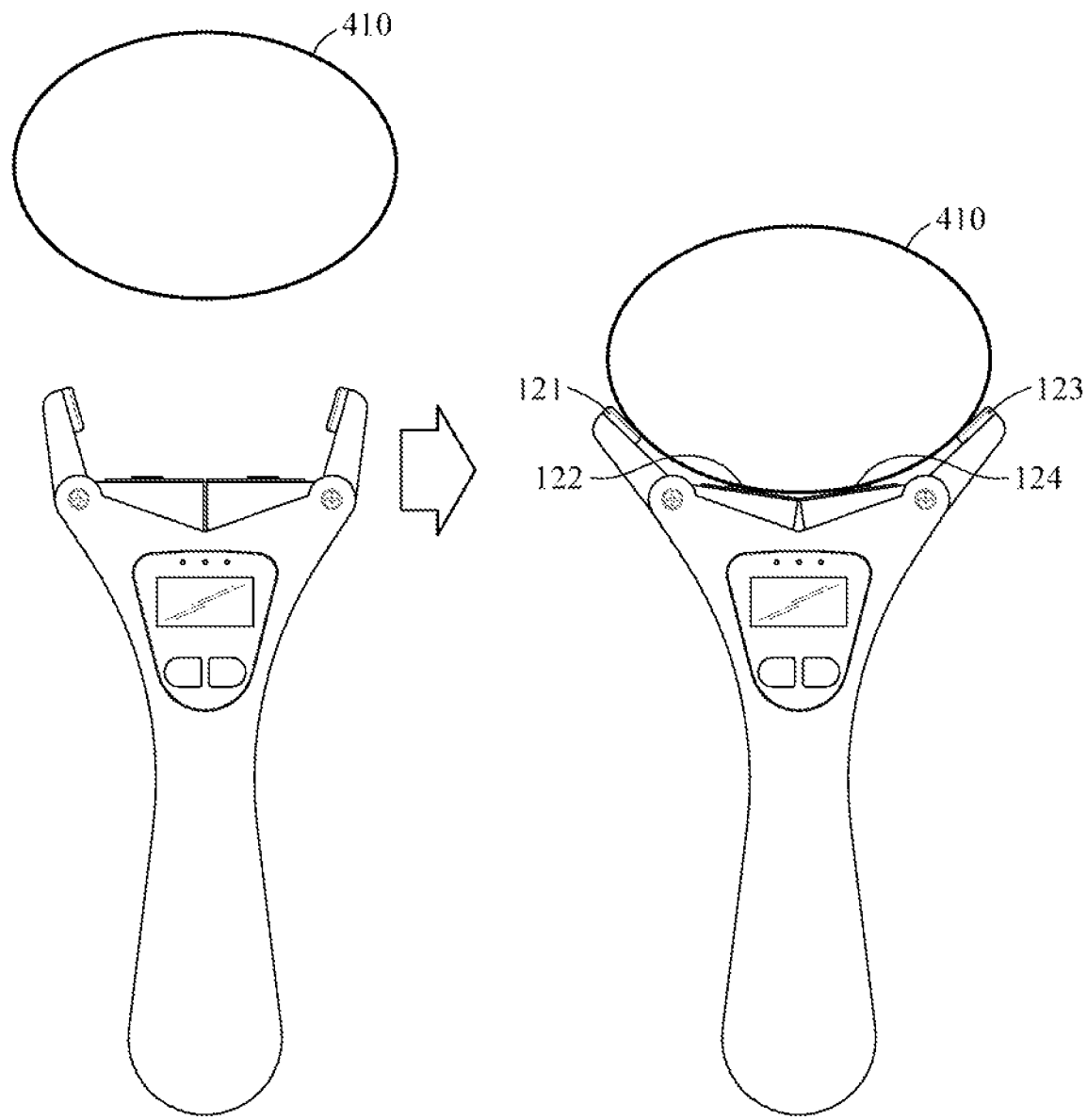
FIG. 4 is a diagram illustrating an operation of a bioimpedance measurement device when pressed by a subject to be measured according to an example embodiment.

FIG. 4 is a diagram illustrating an operation of a bioimpedance measurement device when pressed by a subject to be measured according to an example embodiment.

Referring to FIG. 4, an exemplary situation when a subject to be measured 410 approaches and comes into contact with the plurality of electrodes 121 to 124 is illustrated. In FIG. 4, it is assumed that a circumference of the subject to be measured 410 is greater than a reference value.

When the subject to be measured 410 approaches and comes into contact with the plurality of electrodes 121 to 124, the second electrode 122 may be pressed by the subject to be measured 410 and rotate toward a grip, thereby accommodating the subject to be measured 410 deeper than when the subject to be measured 410 begins to come into contact with the second electrode 122. The fourth electrode 124 may be adjacent to the second electrode 122, and may be pressed by the subject to be measured 410 and rotate toward the grip, thereby accommodating the subject to be measured 410 deeper than when the subject to be measured 410 begins to come into contact with the fourth electrode 124.

In order to measure a bioimpedance of a subject to be measured with high accuracy, it is required for the plurality of electrodes 121 to 124 to come into contact with the subject to be measured with an appropriate pressure. Therefore, it is required to determine whether at least one of the second electrode 122 and the fourth electrode 124 rotates to a limit toward the grip and is pressed, and a bioimpedance measurement result may be determined not to be valid when the at least one rotates to the limit and is pressed.

In addition, the second electrode 122 and the fourth electrode 124 may be independent electrodes, and a degree to which the fourth electrode 124 rotates toward the grip may be different from a degree to which the second electrode 122 rotates toward the grip. However, considering a shape of the subject to be measured for which a bioimpedance is measured, when a difference between the degree to which the second electrode 122 rotates toward the grip and the degree to which the fourth electrode 124 rotates toward the grip is less than or equal to a predetermined threshold, the bioimpedance measurement result may be determined to be valid. For example, when the difference between the degree in which the second electrode 122 rotates toward the grip and the degree in which the fourth electrode 124 rotates toward the grip exceeds the predetermined threshold because the subject to be measured 410 does not properly come into contact, the bioimpedance measurement result may be determined not to be valid, and a message informing re-contact may be outputted, thereby effectively preventing occurrence of biased pressing that is too biased to one side due to improper contact.

Figure 5:
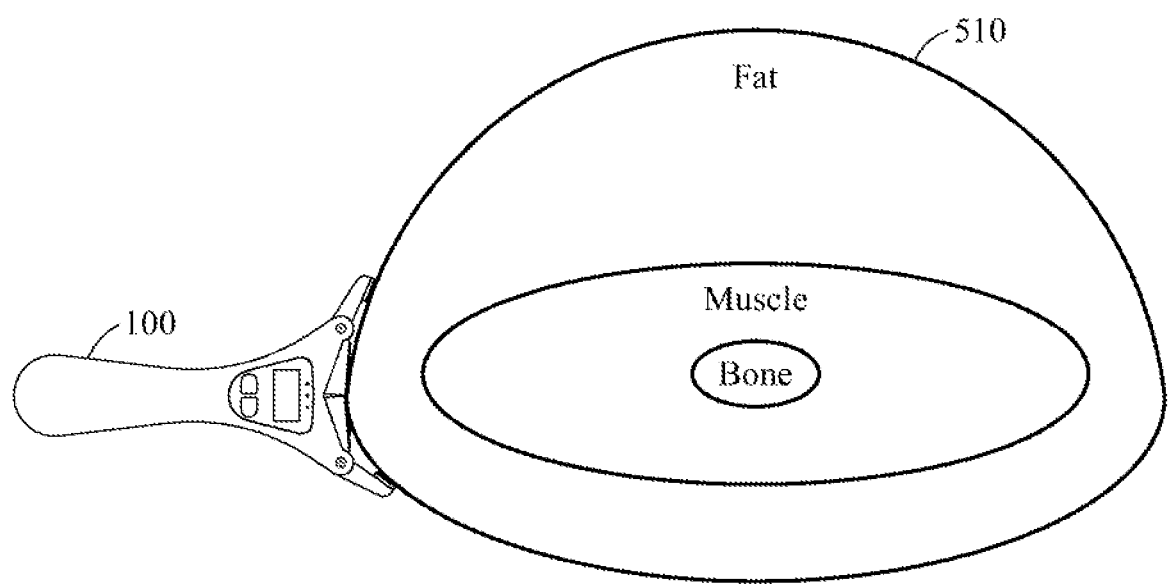
FIGS. 5 to 7 are diagrams illustrating an operation of a bioimpedance measurement device depending on a measurement part according to an example embodiment.
Figure 6:
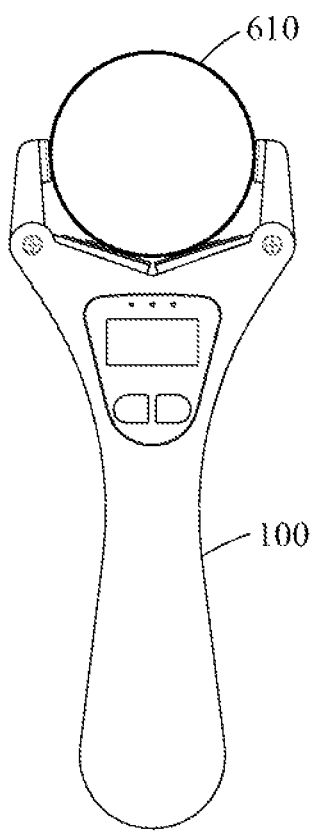
Figure 7:
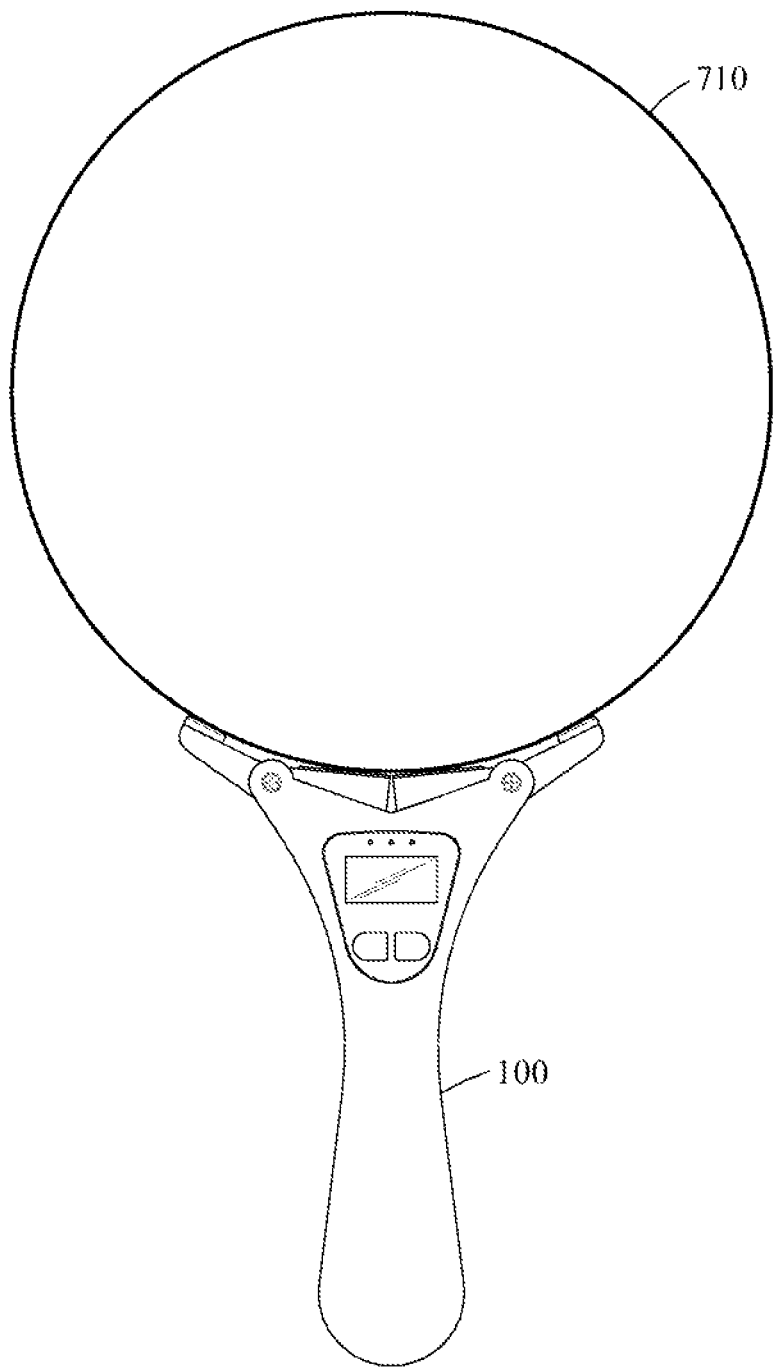

FIGS. 5 to 7 are diagrams illustrating an operation of a bioimpedance measurement device depending on a measurement part according to an example embodiment.

FIG. 5 illustrates an example of measuring a bioimpedance at a waist part 510 of a subject to be measured according to an example embodiment, FIG. 6 illustrates an example of measuring a bioimpedance at an arm part 610 of the subject to be measured according to an example embodiment, and FIG. 7 illustrates an example of measuring a bioimpedance at a thigh part 710 of the subject to be measured according to an example embodiment.

According to an example embodiment, while the subject to be measured approaches and comes into contact with a plurality of electrodes, a measurement circuit provided in the bioimpedance measurement device 100 may estimate a part of the subject to be measured that is in contact using at least one of a degree to which a second electrode rotates toward a grip, a degree to which a fourth electrode rotates toward the grip, a degree to which a first electrode is spread or gathered, and a degree to which a third electrode is spread or gathered.

For example, In FIG. 5 in which the bioimpedance is measured at the waist part 510 of the subject to be measured, considering that a back part is generally flat while a belly part is convex, an upper part of the waist part 510 of the subject to be measured may represent the belly part, and a lower part of the waist part 510 may represent the back part. When the bioimpedance is measured at the waist part 510 of the subject to be measured as illustrated in FIG. 5, a difference may occur between a degree to which an electrode positioned on a belly side of the subject to be measured is spread and a degree to which an electrode positioned on a back side of the subject to be measured is spread, among the first electrode and the third electrode. Based on the difference, the measurement circuit may estimate to be in contact with the waist part of the subject to be measured.

At this time, an estimating device may determine which part of a right side and a left side of the subject to be measured is in contact by comparing the degree to which the first electrode is spread and the degree to which the third electrode is spread. For example, when the degree to which the first electrode is spread is greater than the degree to which the third electrode is spread, the measurement circuit may determine to be in contact with the left side of the subject to be measured. Conversely, when the degree to which the third electrode is spread is greater than the degree to which the first electrode is spread, the measurement circuit may determine to be in contact with the right side of the subject to be measured.

In addition, In FIG. 5, a difference may occur between a degree to which an electrode positioned on the belly side of the subject to be measured rotates toward a grip and a degree to which an electrode positioned on the back side of the subject to be measured rotates toward the grip, among the second electrode and the fourth electrode. Based on the difference, the measurement circuit may estimate to be in contact with the waist part of the subject to be measured. In addition, the estimating device may determine which part of the right side and the left side of the subject to be measured is in contact by comparing a degree to which the second electrode rotates toward the grip and a degree to which the fourth electrode rotates toward the grip. For example, when the degree to which the fourth electrode rotates is greater than the degree to which the second electrode rotates, the measurement circuit may determine to be in contact with the left side of the subject to be measured. Conversely, when the degree to which the second electrode rotates is greater than the degree to which the fourth electrode rotates, the measurement circuit may determine to be in contact with the right side of the subject to be measured.

For example, In FIG. 6 in which a bioimpedance is measured in an arm part 610 of the subject to be measured, when the subject to be measured approaches and comes into contact with the plurality of electrodes, the second electrode and the fourth electrode may rotate toward the grip, and the first electrode and the third electrode may be gathered inward. Based on movements of the plurality of electrodes, the measurement circuit may estimate to be in contact with the arm part of the subject to be measured.

For example, In FIG. 7 in which a bioimpedance is measured in the thigh part 710 of the subject to be measured, when the subject to be measured approaches and comes into contact with the plurality of electrodes, the second electrode and the fourth electrode may rotate toward the grip, and the first electrode and the third electrode may be spread outward. At this time, the first electrode and the third electrode may be spread identically or similarly, unlike the case of FIG. 5. In other words, a difference between the degree to which the first electrode is spread and the degree to which the third electrode is spread may be within a reference range. Based on the movements of the plurality of electrodes, the measurement circuit may estimate to be in contact with the thigh part of the subject to be measured.

According to an example embodiment, while the subject to be measured approaches and comes into contact, the measurement circuit may estimate a circumference of the subject to be measured using at least one of the degree to which the second electrode rotates toward the grip, the degree to which the fourth electrode rotates toward the grip, a degree to which the first electrode is spread or gathered, and a degree to which the third electrode is spread or gathered. Referring to the examples illustrated in FIGS. 6 and 7, the movements of the plurality of electrodes may be different from one another according to the circumference of the subject to be measured. Based on the movements of the plurality of electrodes, the measurement circuit may estimate the circumference of the subject to be measured. In addition, In FIG. 5, the measurement device that determines to be in contact with the waist part of the subject to be measured may estimate a waist circumference of the subject to be measured in consideration of the movements of the plurality of electrodes and a waist shape.

According to an example embodiment, while being pressed by the subject to be measured, the measurement circuit may estimate one of a plurality of predetermined users that corresponds to the subject to be measured using at least one of the degree to which the second electrode rotates toward the grip, the degree to which the fourth electrode rotates toward the grip, the degree to which the first electrode is spread or gathered, and the degree to which the third electrode is spread or gathered. Since a bioimpedance or body circumference hardly changes rapidly, a user whose bioimpedance is currently being measured may be determined by referring to the bioimpedance and body circumference measured in the past. For example, when a father, mother, and daughter living in the same house use the bioimpedance measurement device, the measurement circuit may determine whether a current subject to be measured corresponds to the father, mother, or daughter, based on the movements of the plurality of electrodes.

Figure 8:
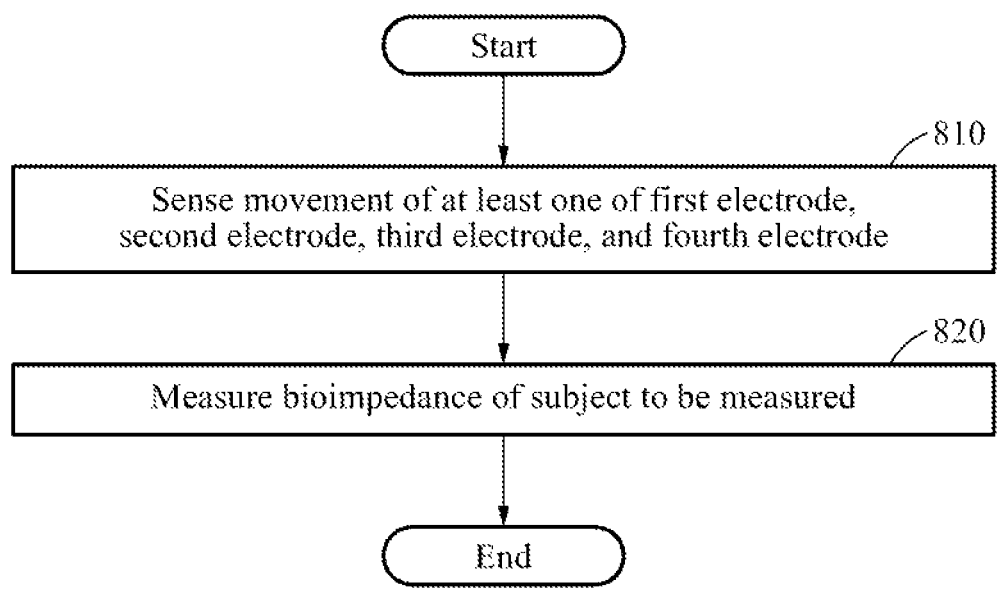
FIG. 8 is a diagram illustrating an operating method of a bioimpedance measurement device according to an example embodiment.

FIG. 8 is a diagram illustrating an operating method of a bioimpedance measurement device according to an example embodiment.

In operation 810, when a subject to be measured approaches the bioimpedance measurement device, and is surrounded by and comes into contact with the bioimpedance measurement device, the bioimpedance measurement device may sense a movement of at least one of a first electrode, a second electrode, a third electrode, and a fourth electrode provided in the bioimpedance measurement device. The first electrode and the second electrode may be coupled to a first shaft provided on one side of the bioimpedance measurement device to rotate about the first shaft. The third electrode and the fourth electrode may be coupled to a second shaft on the one side of the bioimpedance measurement device at a position different from that of first shaft to rotate about the second shaft.

In addition, while the subject to be measured approaches and comes into contact, the bioimpedance measurement device may estimate a circumference of the subject to be measured using at least one of a degree to which a second electrode rotates toward a grip, a degree to which a fourth electrode rotates toward the grip, a degree to which a first electrode is spread or gathered, and a degree to which a third electrode is spread or gathered.

In addition, while being pressed by the subject to be measured, the bioimpedance measurement device may estimate a part of the subject to be measured that is in contact by comparing the degree to which the second electrode rotates toward the grip and the degree to which the fourth electrode rotates toward the grip.

In addition, while being pressed by the subject to be measured, the bioimpedance measurement device may estimate a part of the measurement subject that is in contact by comparing a degree to which the first electrode is spread and a degree to which the third electrode is spread.

In addition, while being pressed by the subject to be measured, the bioimpedance measurement device may determine that a bioimpedance measurement result when a difference between the degree to which the second electrode rotates toward the grip and the degree to which the fourth electrode rotates toward the grip is less than or equal to a predetermined threshold is valid.

In addition, while the subject to be measured approaches and comes into contact, the bioimpedance measurement device may estimate a part of the subject to be measured that is in contact using at least one of the degree to which the second electrode rotates toward the grip, the degree to which the fourth electrode rotates toward the grip, the degree to which the first electrode is spread or gathered, and the degree to which the third electrode is spread or gathered.

In addition, while the subject to be measured approaches and comes into contact, the bioimpedance measurement device may estimate one of a plurality of predetermined users that corresponds to the subject to be measured using at least one of the degree to which the second electrode rotates toward the grip, the degree to which the fourth electrode rotates toward the grip, the degree to which the first electrode is spread or gathered, and the degree to which the third electrode is spread or gathered.

In addition, while being pressed by the subject to be measured, the bioimpedance measurement device may determine that the bioimpedance measurement result is not valid when at least one of the second electrode and the fourth electrode rotates to a limit toward the grip and is pressed.

In operation 820, the bioimpedance measurement device may measure a bioimpedance of the subject to be measured using at least one of the first electrode, the second electrode, the third electrode, and the fourth electrode. For example, the bioimpedance measurement device may measure the bioimpedance of the subject to be measured after the sensed movements of the plurality of electrodes are terminated. In addition, the bioimpedance measurement device may determine a body composition of the subject to be measured based on the bioimpedance and circumference of the subject to be measured.

The details described above with reference to FIGS. 1 to 8 are applied to respective operations illustrated in FIG. 8, and thus a more detailed description is omitted.

Figure 9:
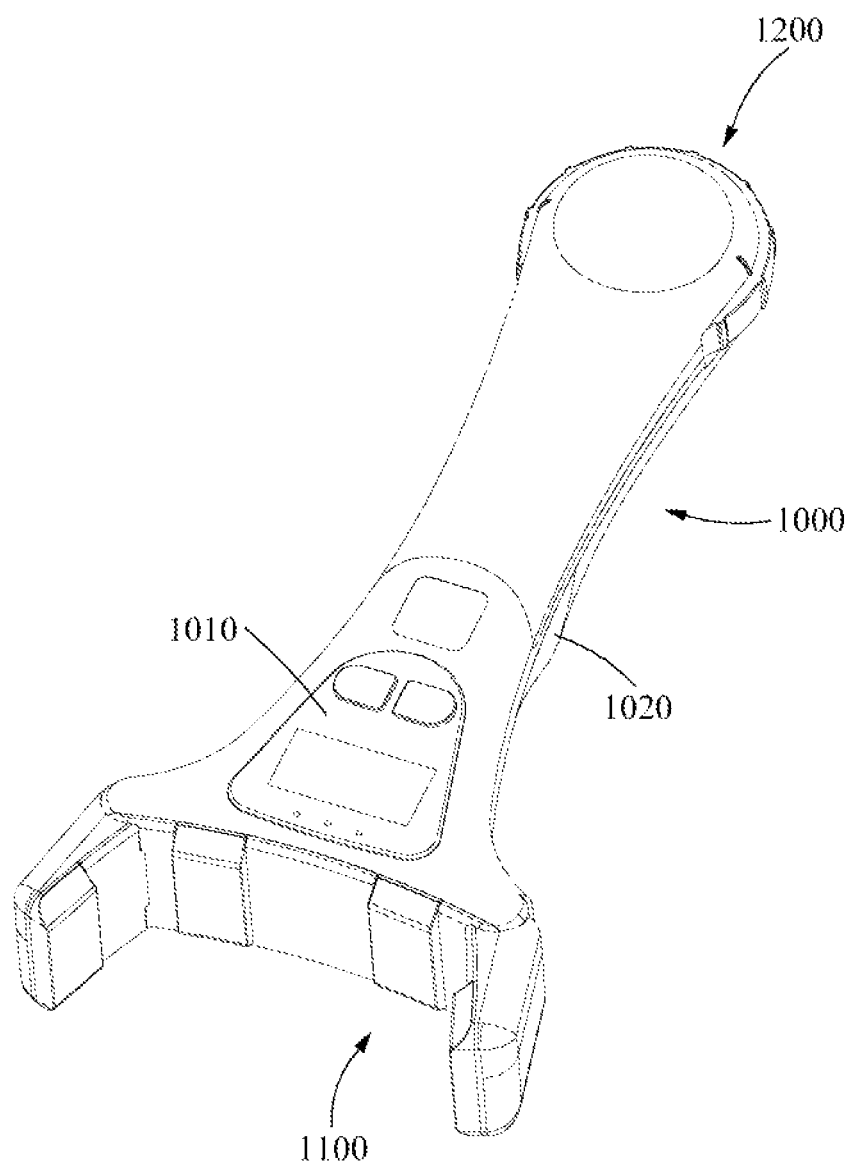
FIG. 9 is a perspective diagram of an impedance measurement device according to an example embodiment.

FIG. 9 is a perspective diagram of an impedance measurement device according to an example embodiment.

Referring to FIG. 9, a measurement device 900 may include a body 1000, a sample part 1100, and a length measurement part 1200.

The body 1000 may include a gripping surface, and the body 1000 may be gripped by one hand through the gripping surface. The body 1000 may have a T-shape or a Y-shape, but the shape is not limited thereto, and any shape is possible as long as the body part 1000 may be gripped by one hand. The body 1000 may include an upper cover and a lower cover, and the upper cover and the lower cover may be coupled to each other or separated from each other. The upper cover and the lower cover of the body 1000 may be made of PC+ABS material, but are not necessarily limited thereto and may be made of any known material.

The sample part 1100 may be coupled to one side of the body 1000, and the length measurement part 1200 may be coupled to another side of the body 1000, but are not limited to a specific position and may be provided in an additional body. According to the present disclosure, one device may include both the sample part 1100 that measures an impedance and the length measurement part 1200 that measures a circumference or length of a measurement part, and thus a bioimpedance may be measured and calculated with the one device without a need for an additional device. In addition, a body composition may be measured and calculated based on a measured impedance value and a measured circumference or length value of the measurement part, only with the measurement device. However, in order to further increase precision and accuracy in body composition measurement, it is possible to link with another body composition measurement equipment.

Alternatively, two electrodes positioned at opposite ends among four electrodes included in the sample part 1100 may be spread in opposite lateral directions while being in close contact with an examinee. At this time, angle sensors that measure a degree of rotation of the two electrodes that are spread in opposite lateral directions may be further provided. In this case, a circumference or length of the examinee may be determined based on the degree of rotation measured by the angle sensor.

The measurement device 900 may further include a measurement circuit and a controller.

The measurement circuit may be included in the body 1000 of the measurement device 900. The measurement circuit may measure an impedance of the examinee through the electrodes of the sample part 1100. The measurement circuit may calculate an amount of body fat based on the measured impedance.

The controller may receive a numerical value for the calculated amount of body fat and display the numerical value through a liquid crystal part 1013 of a display part 1010. The controller may receive a length or circumference value measured by the length measurement part 1200 and display the length or circumference value on the liquid crystal part 1013 of the display part 1010.

Figure 10A:
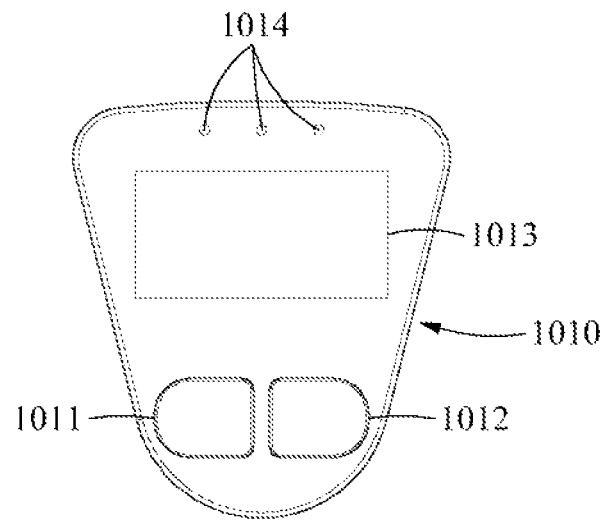
FIGS. 10A and 10B are schematic diagrams illustrating a configuration of a body of a bioimpedance measurement device according to an example embodiment.
Figure 10B:
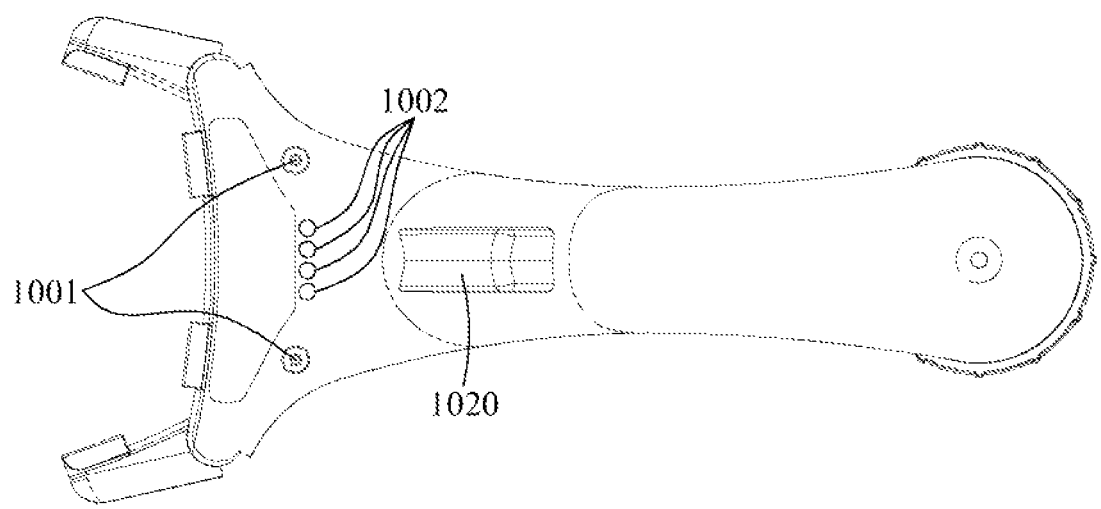

FIGS. 10A and 10B are schematic diagrams illustrating a configuration of a body of a bioimpedance measurement device according to an example embodiment.

Referring to FIGS. 10A and 10B, the body 1000 may include the display part 1010, a fixing part 1001, and a charging/communication terminal 1002.

The display part 1010 may be disposed on an outer surface of an upper cover of the body 1000, and may include a first button 1011, a second button 1012, the liquid crystal part 1013, and an LED lamp 1014.

The first button 1011 may serve to initialize existing measurement data. In order to obtain data by a new measurement, the existing data may be initialized by clicking the first button before measurement. After a circumference is measured by the length measurement part 1200, the first button may be clicked to measure an impedance, and then the impedance may be measured by the sample part 1100.

The second button 1012 may provide a function capable of mode conversion between a plurality of modes including a first mode for measuring an impedance and a second mode for measuring a circumference or length of an examinee.

However, functions of the first button 1011 and the second button 1012 are not limited to those described above, and the display part 1010 may further include a button having another function.

In the first mode, the liquid crystal part 1013 may display whether an electrode of the sample part to be described later properly comes into contact with the examinee, an impedance measurement value, and the like. In the second mode, a circumference or length of a measurement part may be displayed. According to another example embodiment of the present disclosure, the liquid crystal part 1013 may further display an additional third mode, and in the third mode, not only the impedance measurement value but also an amount of body fat and a percentage of body fat may be displayed, an amount of each of subcutaneous fat and visceral fat may be displayed, and an overall degree of obesity may be displayed.

According to the LED lamp 1014, it is possible to determine, by a pressure sensor attached to the electrode to be described later, whether the electrode comes into contact with the examinee while applying an appropriate pressure to the examinee. It is possible to determine whether the examinee appropriately comes into contact with the electrode by measuring a pressure applied to the electrode so as to accurately measure an impedance of the examinee. By lighting of the LED lamp 1014, it is possible to identify whether the examinee appropriately comes into contact with the electrode. The number of LED lamps 1014 is illustrated as three, but is not limited thereto.

A pressure display part that displays a degree of pressure of the electrode that comes into contact with the examinee may be displayed through various means and methods in addition to the LED lamp 1014 which is one of the above-described example embodiments. For example, the pressure applied to the electrode by the examinee may be displayed on the liquid crystal part 1013 of the display part 1010 as a pressure gauge. For example, the pressure applied to the electrode may be displayed on the liquid crystal part 1013 through, for example, a gauge displayed as a bar. Accordingly, a user may appropriately adjust the pressure applied to the electrode with reference to displayed pressure information to smoothly measure the impedance of the examinee.

The fixing part 1001 may allow the measurement device not to be easily separated when the measurement device is mounted on an additional charger, and may be made of a material having a magnetic property. The charging/communication terminal 1002 may electrically connect a power supply source and the measurement device to each other when power of the measurement device is charged.

FIGS. 11A to 12C are schematic diagrams illustrating various example embodiments of a sample part of a bioimpedance measurement device according to an example embodiment.

The sample part 1100 may be coupled to one side of the body 1000. The sample part 1100 may include a plurality of segment members and a plurality of electrodes. An electrode may be disposed on one surface of the plurality of segment members. The plurality of segment members may be rotatably coupled to one another, and an angle may be adjusted depending on a measurement part or a body shape. Accordingly, an impedance may be measured regardless of a shape of the measurement part or the body shape. The plurality of electrodes may include an electrode for applying a current and an electrode for measuring a voltage.

Figure 11A:
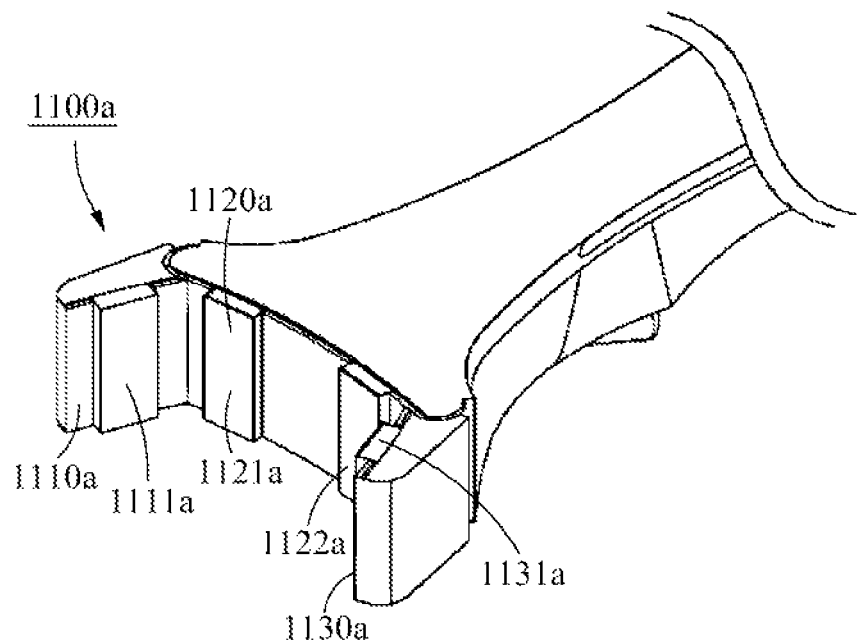
FIGS. 11A to 12C are schematic diagrams illustrating various example embodiments of a sample part of a bioimpedance measurement device according to an example embodiment.

Referring to a sample part 1100a according to a first example embodiment of the present disclosure, referring to FIG. 11A, the sample part 1100a may include a plurality of segment members 1110a to 1130a and electrodes 1111a to 1131a disposed on one surface of respective segment members. The first segment member 1110a to the third segment member 1130a may be rotatably coupled to one another. The number of segment members is not limited to three illustrated in FIG. 11A.

The second segment member 1120a may be coupled to the one side of the body 1000, and may have one surface on which one or more pairs of electrodes are disposed. However, the number of disposed electrodes is not limited thereto. The first segment member 1110a and the third segment member 1130a may be rotatably coupled to opposite ends of the second segment member 1120a, and may have one surface on which one or more electrodes are disposed. However, the number of disposed electrodes is not limited thereto. The electrode may include one or more pairs of electrodes for applying a current and one or more pairs of electrodes for measuring a voltage. The sample part 1100a according to the first example embodiment may be connected to an angle adjustment part 10 to be described later, so that an angle of each segment member may be adjusted by the angle adjustment part 10, but the angle of each segment member may be adjusted without being connected to the angle adjustment part 10.

Figure 11B:
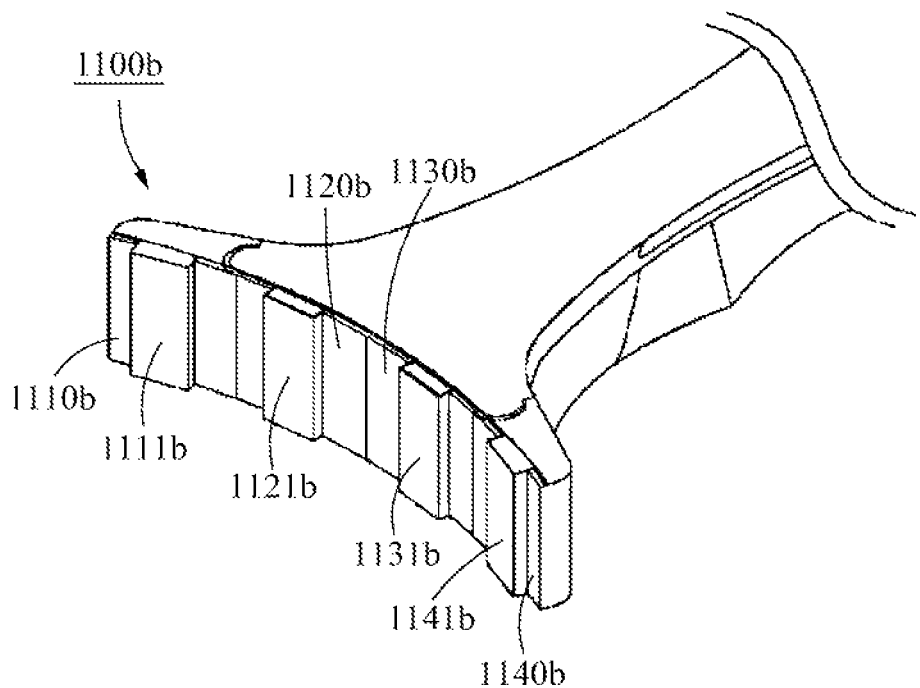

According to a sample part 1100b according to a second example embodiment of the present disclosure, referring to FIG. 11B, the sample part 1100b may include a plurality of segment members 1110b to 1140b and electrodes hub to 1141b disposed on one surface of respective segment members. The first segment member 1110b to the fourth segment member 1140b may be rotatably coupled to one another. The number of segment members is not limited to four illustrated in FIG. 11B.

The second segment member 1120b and the third segment member 1130b may be coupled to the one side of the body 1000, and may have one surface on which one or more electrodes are disposed, but the number of disposed electrodes is not limited thereto. The first segment member 1110b and the fourth segment member 1140b may be rotatably coupled to the second segment member 1120b and the third segment member 1130b, respectively, and may have one surface on which one or more electrodes are disposed, but the number of disposed electrodes is not limited thereto. The sample part 1100b according to the second example embodiment may be connected to the angle adjustment part 10 to be described later, so that an angle of each segment member may be adjusted by the angle adjustment part 10, but the angle of each segment may be adjusted without being connected to the angle adjustment part 10.

Figure 12A:
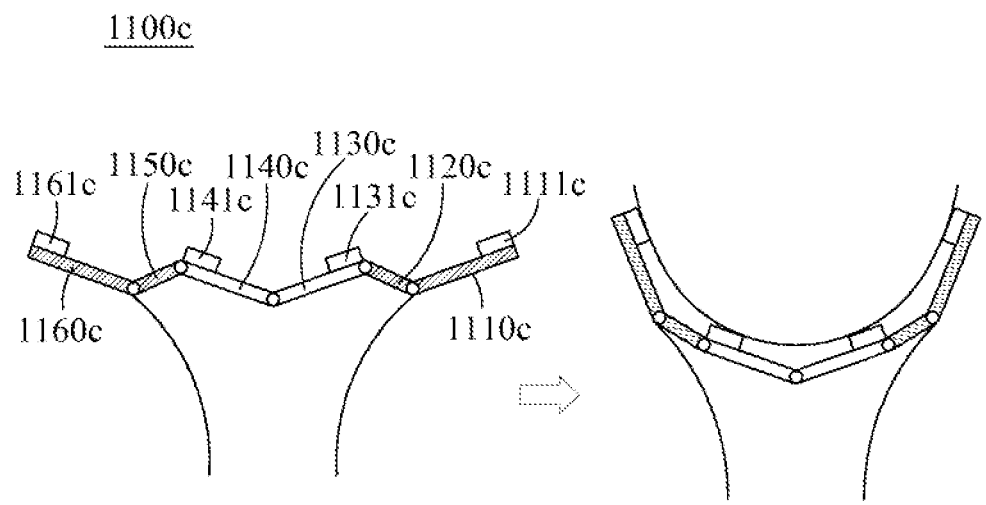

According to a sample part 1100c according to a third example embodiment of the present disclosure, referring to FIG. 12A, the sample part 1100c may include a plurality of segment members 1110c to 1160c and electrodes 1111c, 1131c, 1141c and 1161c disposed on one surface of respective segment members. The first segment member 1110c to the sixth segment member 1160c may be rotatably coupled to one another. A hinge part to which the first segment member 1110c and the second segment member 1120c are connected and a hinge part to which the fifth segment member 1150c and the sixth segment member 1160c are connected may be coupled to the body 1000, but are not limited thereto, and another hinge part may be coupled to the body. The number of segment members is not limited to six illustrated in FIG. 12A.

In the sample part 1100c according to the third example embodiment, each segment member may be maintained in a state illustrated in a left figure of FIG. 12A by an elastic body (not illustrated) or the like.

The sample part 1100c according to the third example embodiment may be connected to the angle adjustment part 10 to be described later, so that an angle of each segment member may be adjusted by the angle adjustment part 10, but the angle of each segment member may be adjusted without being connected to the angle adjustment part 10. Referring to a right figure of FIG. 12A, when the second electrode 1131c and the third electrode 1141c of the sample part 1100c are brought into contact with an examinee, the first segment member 1110c and the sixth segment member 1160c may rotate and come into contact with the examinee. When the sample part 1100c is detached from the examinee, the sample part 1100c may return to an initial state as illustrated in the left figure of FIG. 12A.

Figure 12B:
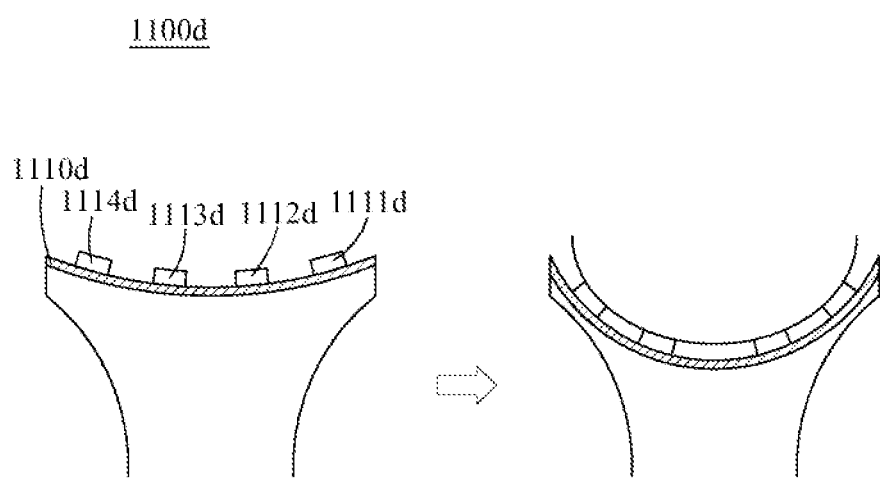

According to a sample part 1100d according to a fourth example embodiment of the present disclosure, referring to FIG. 12B, the sample part 1100d may include one sample member 1110d and electrodes 1111d, 1112d, 1113d and 1114d disposed on one surface of the sample member 1110d. The number of sample members 1110d is not limited to one illustrated in FIG. 12B, and a plurality of segmented sample members 1110d may be further included.

The sample member 1110d of the sample part 1100d according to the fourth example embodiment may be made of an elastic material, and as the sample member 1110d is pressed, the sample member 1110d may be bent in a bow shape in a direction of the body 1000. The sample member 1110d may be maintained in a state illustrated in a left figure of FIG. 12B. When the sample part 1110d is brought into contact with an examinee, the sample member 1110d may be bent in a bow shape as illustrated in a right figure of FIG. 12B in accordance with a shape and size of the examinee, and all of electrodes 1111d to 1114d may come into contact with the examinee. When the sample part 1100d is detached from the examinee, the sample part 1100d may return to an initial state as illustrated in the left figure of FIG. 12B. The sample part 1100d may be connected to the angle adjustment part 10 to be described later, so that a radius of curvature or angle of the sample member 1110d on which the electrodes are disposed may be adjusted by the angle adjustment part 10 so that all electrodes are in contact with the examinee. However, the radius of curvature or angle of the sample member 1110d may be adjusted by bring the sample member 1110d made of an elastic material into contact with the examinee to allow the sample member 1110d to be bent, without being connected to the angle adjustment part 10.

Figure 12C:
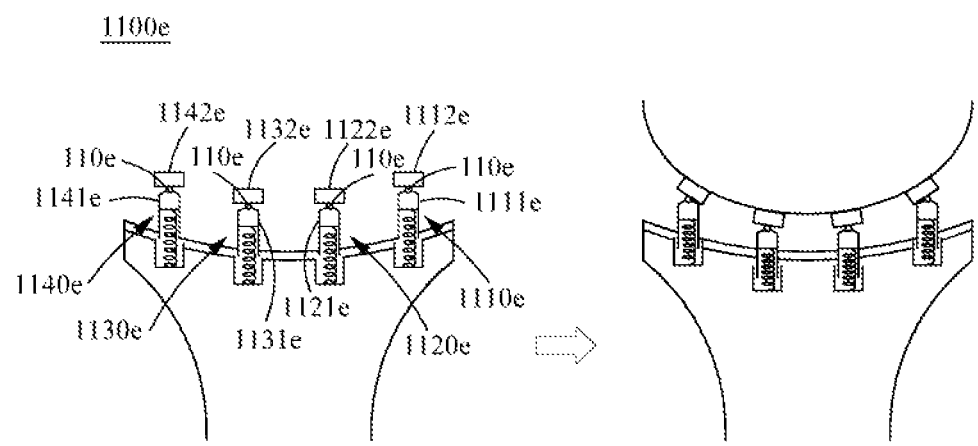

According to a sample part 1100e according to a fifth example embodiment of the present disclosure, referring to FIG. 12C, the sample part 1100e may include a plurality of first to fourth sample members 1110e to 1140e. However, the number of sample members is not limited to four illustrated in FIG. 12C.

Since each sample member includes the same component, a common part is described below mainly with respect to the first sample member 1110e.

The first sample member 1110e may include a first pillar member 1111e, an electrode angle adjustment member 110e, and a first electrode 1112e.

The first pillar member hue may be a hollow member. The first pillar member 1111e may include an elastic body within a hollow interior. In this case, the elastic body may be anything known, and may be, for example, a spring. The first pillar member 1111e may move in a direction of compressing the elastic body as electrodes come into contact with an examinee. When the electrodes do not come into contact with the examinee, the elastic body may be relaxed, and the first pillar member 1111e may return to an initial state as illustrated in a left figure of FIG. 12C.

The electrode angle adjustment member 110e may adjust angles of electrodes 1112e to 1142e that come into contact with the examinee. The electrode angle adjustment member 110e may be, for example, a known ball bearing, but is not limited thereto, and anything is possible as long as it is capable of adjusting an angle of an electrode that comes into contact with the examinee. According to the electrode angle adjustment member 110e, when the electrode is brought into contact with the examinee, as illustrated in a right figure of FIG. 12c, respective pillar members hue to 1241e may move in a direction of compressing the elastic body included therein, and the angles of respective electrodes 1112e to 1142e may be adjusted to correspond to a shape of the examinee. When the sample part 1100e is detached from the examinee, the sample part 1100e may return to an initial state as illustrated in the left figure of FIG. 12C. The sample part 1100e may be connected to the angle adjustment part 10 to be described later, so that angles of respective electrodes may be adjusted by the angle adjustment part 10 so that all electrodes are in contact with the examinee. However, the angles of the respective electrodes may be adjusted by the electrode angle adjustment member 110e so that all electrodes come into contact with the examinee merely by applying a certain degree of pressure to the examinee to bring the electrodes into contact with the examinee, without being connected to the angle adjustment part 10.

Both of the electrodes 1121a and 1122a (in the first example embodiment) disposed at the center of the sample parts 1100a to 1100e according to the first to fifth example embodiments may be electrodes for measuring a voltage. However, both of the electrodes 1121a and 1122a (in the first example embodiment) positioned at the center of the sample part 1100 may not need to be electrodes for measuring a voltage, and in some cases, at least one electrode may be an electrode for applying a current.

The electrodes that come into direct contact with the examinee may be made of any known material, but preferably may be made of an ABS material. The electrodes may be plated with chrome on a surface thereof. However, a plating material is not limited to chrome, and any material may be plated as long as it does not cause skin allergies or the like by direct contact with the examinee.

Respective segment members of the sample part 1100 may be made of a PC+ABS material, but is not limited thereto and may be made of any known material.

The sample part 1100 may further include a sample part cover. In the sample part 1100a according to the first example embodiment, the sample part cover may be coupled to each of outer surfaces of the first segment member 1110a and the third segment member 1130a of the sample part 1100a. In the sample part 1100b according to the second example embodiment, the sample part cover may be coupled to each of outer surfaces of the first segment member 1110b and the fourth segment member 1140b. The sample part cover may be made of PC+ABS material, but is not limited thereto and may be made of any known material.

At least some of the electrodes may include a pressure sensor disposed on one side of the electrode. The pressure sensor may be a film-type pressure sensor disposed between the electrode and the sample part 1100. However, a position is not limited thereto, and any position suitable for measuring a pressure applied to the electrode by the examinee is possible. At least some of the electrodes may include the pressure sensor, but preferably, the electrodes 1121a and 1122a (in the first example embodiment) positioned at the center of the sample part 1100 may include the pressure sensor. When at least some of the electrodes come into contact with the examinee, the electrode may be retracted inward, and at this time, it is possible to identify whether the examinee comes into contact with the electrode by the pressure sensor disposed on the one side of the electrode being pressured, and whether the electrode presses the examinee with a degree of pressure required to accurately measure an impedance. At least some of the electrodes may include an elastic material on one side or inside thereof. According to the elastic material, when the examinee comes into contact with the electrode, the electrode is pressed and retracted inward, the pressure sensor disposed on the one side of the electrode is pressed to measure a pressure, and the examinee is detached from the electrode after pressure measurement and impedance measurement are terminated, the electrode may be positioned to an initial state before the pressure sensor is pressed.

After the pressure is measured by the pressure sensor, the pressure measured by the pressure sensor may be displayed through a pressure display part. The pressure display part may be, for example, a pressure gauge displayed on the liquid crystal part 1013 or the LED lamp 1014 additionally installed in the body. The pressure may be displayed as a pressure gauge through the liquid crystal part 1013 of the display part 1010, and whether the electrode properly comes into contact with the examinee may be displayed. In addition, as described above, the pressure may be displayed not only through the liquid crystal part 1013 of the display part 1010, but also through the LED lamp 1014.

When an appropriate level of pressure is measured by the pressure sensor, the measurement device 900 may be configured to determine that the electrode appropriately comes into contact with the examinee, and automatically measure an impedance of the examinee through a measurement circuit. That is, the measurement device 900 may be configured to measure the impedance when the pressure is greater than or equal to a certain level of pressure (a predetermined threshold value).

Accordingly, it is possible to prevent a measurement value of the impedance from being measured differently every time due to a user's inconsistent operation, thereby improving precision and accuracy in impedance measurement.

Figure 13A:
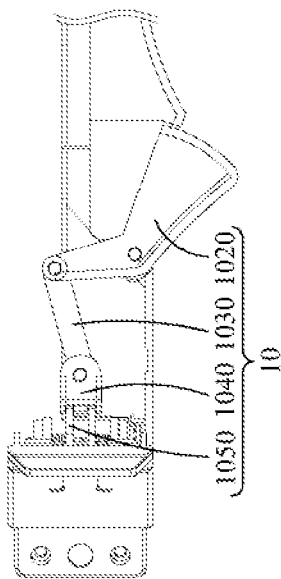
FIGS. 13A and 13B are perspective diagrams illustrating a detailed configuration of an angle adjustment part that is an example embodiment of a means for adjusting an angle of a sample part of a bioimpedance measurement device according to an example embodiment.
Figure 13A:
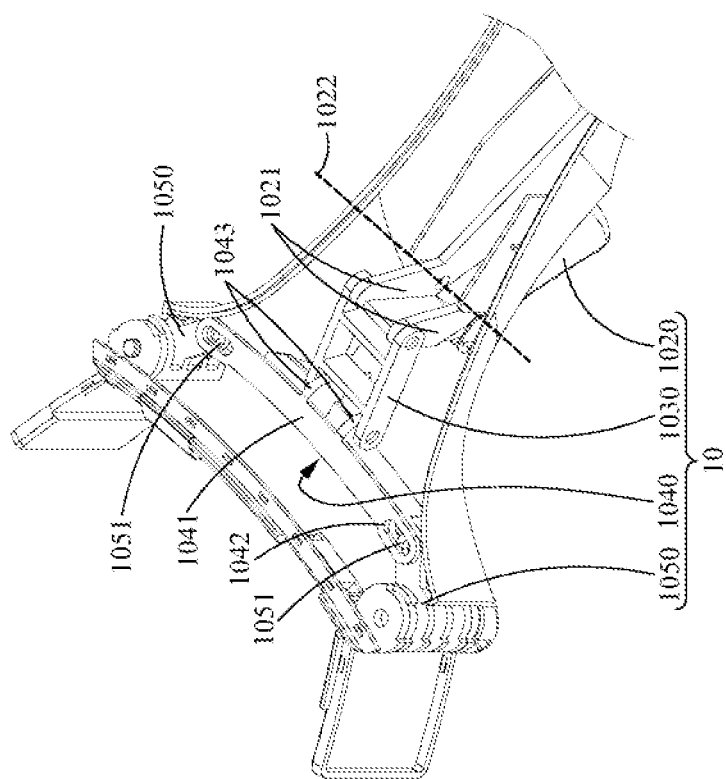
Figure 13B:
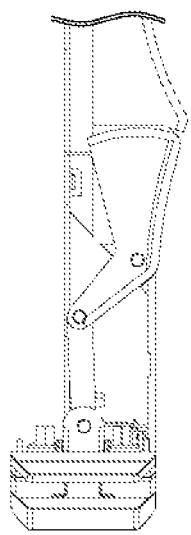
Figure 13B:
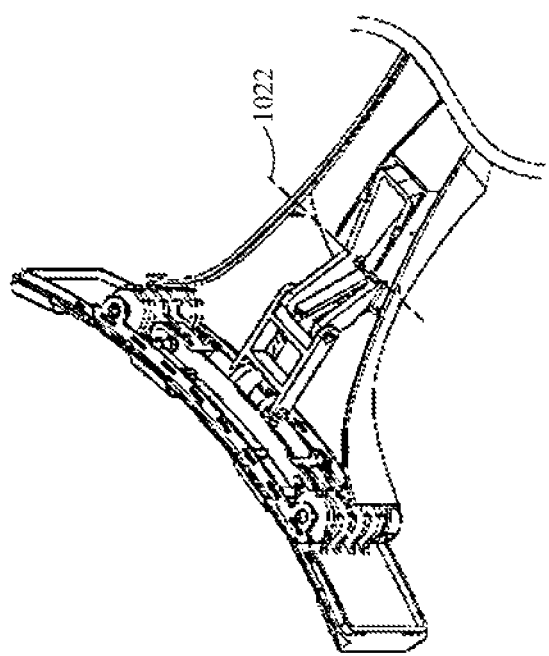

FIGS. 13A and 13B are perspective diagrams illustrating a detailed configuration of an angle adjustment part that is an example embodiment of a means for adjusting an angle of a sample part of a bioimpedance measurement device according to an example embodiment.

FIGS. 13A and 13B, the bioimpedance measurement device according to the present disclosure may further include an angle adjustment part 10 that is a means for adjusting an angle of the sample part 110.

The angle adjustment part 10 may include an adjustment mechanism 1020, a first connector 1030, a second connector 1040, and a rotational coupling part 1050. The angle adjustment part 10 may serve to adjust an angle between segment members of the sample part 1100.

The adjustment mechanism 1020 may be coupled to an inner surface of a lower cover of the body 1000, and may be rotatably coupled to the inner surface about a rotational shaft 1022. The adjustment mechanism 1020 may penetrate through the lower cover of the body 1000 and protrude from the outer surface of the lower cover. When the adjustment mechanism 1020 is pressed or a pressure applied to the adjustment mechanism 1020 is released, the adjustment mechanism 1020 may rotate about the rotational shaft 1022, and a plurality of connecting leg parts 1021 may be connected to the first connector 1030 to be described later to allow the first connector 1030 to perform a reciprocating motion. The plurality of connecting leg parts 1021 may be rotatably coupled to the first connector 1030 to be described later. The adjustment mechanism 1020 may be made of PC+ABS material, but is not limited thereto, and may be made of any known material as long as it has durability or abrasion resistance capable of withstanding repeated movements by a user's operation.

The first connector 1030 may have the adjustment mechanism 1020 coupled to one side thereof and the second connector 1040 coupled to another side thereof. The first connector 1030 may serve as an intermediate leg that connects the adjustment mechanism 1020 and the second connector 1040 to each other. When the adjustment mechanism 1020 is pressed or a pressure applied to the adjustment mechanism 1020 is released, the first connector 1030 may perform a linear reciprocating motion. A shape of the first connector 1030 may be a " Π " shape or "H" shape, but is not limited thereto, and any shape is possible as long as it is capable of connecting the adjustment mechanism 1020 and the second connector 1040 to each other. The first connector 1030 may be made of a POM material, but is not limited thereto, and may be made of any material as long as it has durability or abrasion resistance capable of withstanding repeated movements.

The second connector 1040 may include a linear motion member 1041 including a plurality of coupling grooves 1042 and a connecting member 1043.

The linear motion member 1041 may perform a linear reciprocating motion by the first connector 1030 that performs a linear reciprocating motion as the adjustment mechanism 1020 is pressed or a pressure applied to the adjustment mechanism 1020 is released. As the linear motion member 1041 performs a linear reciprocating motion, the rotational coupling part 1050 to be described later may perform a rotational motion. The plurality of coupling grooves 1042 may be formed on opposite longitudinal sides of the linear motion member 1041. One side of the rotational coupling part 1050 to be described later may be coupled to the plurality of coupling grooves 1042. The linear motion member 1041 may have a horizontally elongated curved bar shape, but is not limited thereto, and any shape is possible as long as it is capable of rotating the rotational coupling part 1050 to be described later by performing a linear reciprocating motion.

The connecting member 1043 may be disposed on a bottom surface of the linear motion member 1041 to couple the second connector 1040 and the first connector 1030 to each other. The connecting member 1043 may be coupled to another side of the first connector 1030, and may be rotatably coupled to the other side of the first connector 1030.

The second connector 1040 may be made of a POM material, but is not limited thereto, and may be made of any material as long as it has durability or abrasion resistance capable of withstanding repeated linear reciprocating motions.

The rotational coupling part 1050 may rotate about a rotational shaft. The rotational coupling part 1050 may be disposed as a pair of left and right rotational coupling parts, but is not limited thereto. The rotational coupling part 1050 may be coupled to each segment member of the sample part 1100. In the sample part 1100*a* according to the first example embodiment of the present disclosure, a first segment member 1110 and a third segment member 1130 may be coupled to the rotational coupling part 1050. In the sample part 1100*b* according to the second example embodiment of the present disclosure, the first segment member 1110 and a fourth segment member 1140 may be coupled to the rotational coupling part 1050. As the rotational coupling part 1050 rotates, each segment member coupled to the rotational coupling part 1050 may rotate.

The rotational coupling part 1050 may be coupled to the second connector 1040. A protrusion 1051 may be formed on the one side of the rotational coupling part 1050, and the protrusion 1051 may slide in a longitudinal direction of the coupling groove 1042 to be coupled in a manner capable of performing a reciprocating motion. When the adjustment mechanism 1020 is not pressed, the protrusion 1051 may be positioned on the outside of the coupling groove 1042. When the adjustment mechanism 1020 is pressed and the second connector 1040 performs a linear motion to be closer to the sample part 1100, the rotational coupling part 1050 may rotate, and the protrusion 1051 of the rotational coupling part 1050 may slidingly move from the outside to the inside of the coupling groove 1042. Accordingly, respective segment members of the sample part 1100 coupled to the rotational coupling part 1050 may rotate. In the sample part 1100*a* according to the first example embodiment of the present disclosure, the first segment member 1110 and the third segment member 1130 each may rotate to change (for example, increase or decrease) an angle with the second segment member 1120. In the sample part 1100*b* according to the second example embodiment of the present disclosure, the first segment member 1110 to the fourth segment member 1140 may rotate to change an angle between all segment members coupled to one another.

The rotational coupling part 1050 may be made of a POM material, but is not limited thereto, and may be made of any material as long as it has durability or abrasion resistance capable of withstanding repeated rotational motions.

The rotational coupling part 1050 may include an elastic body therein. When the adjustment mechanism 1020 is not pressed by the elastic body included therein, each segment member coupled to each rotational coupling part 1050 may be maintained in a state of being retracted inward. A general spring may be used as the elastic body, but is not limited thereto, and any suitable material may be used as long as it is capable of maintaining a state in which each segment member is retracted inward when the adjustment mechanism 1020 is not pressed.

After an angle between respective segment members is changed by pressing the adjustment mechanism 1020, at least some of a plurality of segment members may be brought into contact with a measurement part of an examinee, and then a state of pressing the adjustment mechanism 1020 may be released to adjust the angle between respective segment members to be decreased, thereby allowing remaining segment members that do not come into contact with the examinee to come into contact with the examinee. That is, an impedance may be measured by allowing the electrode to come into contact with all parts of the examinee. Accordingly, since the angle between the respective segment members is adjusted to correspond to a shape or thickness of the examinee so that all of the plurality of segment members come into contact with the examinee, the impedance may be measured regardless of the shape or thickness and the measurement part of the examinee. At this time, segment members that come into contact with the examinee later may press the examinee with a pressure caused by a spring disposed inside the rotational coupling part 1050. That is, accordingly, the segment members may come into contact with the examinee with a constant pressure caused by the spring regardless of the shape or thickness and the measurement part of the examinee, thereby improving precision and accuracy in impedance measurement.

The angle adjustment part 10 may be applied to be connected to the sample part 1100*a* according to the first example embodiment and the sample part 1100*b* according to the second example embodiment, but is not limited thereto, and may be also applied to be connected to sample parts the third to fifth example embodiments, so that an angle of each segment member or each electrode, and an angle or a radius of curvature of a sample member may be adjusted by the angle adjustment part 10.

The angle adjustment part 10 is merely one example embodiment of an adjustment means for adjusting an angle between the respective segment members of the sample part 1100, and as described above, depending on each example embodiment of the sample part 1100, an angle of each segment member or each electrode of the sample part 1100, and an angle or a radius of curvature of a sample member may be adjusted without the angle adjustment part 10.

Figure 14A:
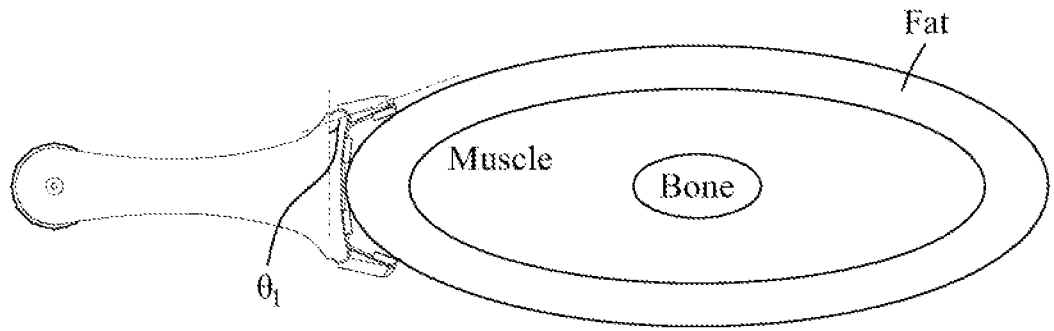
FIGS. 14A and 14B are schematic diagrams illustrating a state in which a bioimpedance is measured by a bioimpedance measurement device according to the present disclosure.
Figure 14B:
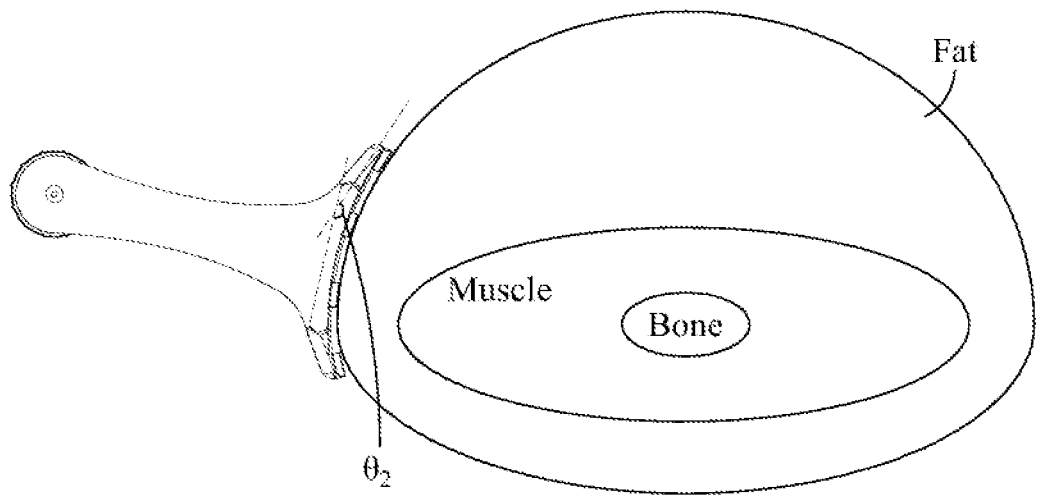

FIGS. 14A and 14B are schematic diagrams illustrating a state in which a bioimpedance is measured by a bioimpedance measurement device according to the present disclosure.

Referring to FIGS. 14A and 14B, it can be seen that an angle between respective segment members of the sample part 1100 varies depending on a body shape or a measurement part.

Referring to FIG. 14A, as a case in which the body shape or the measurement part is relatively thin, a first segment member 1110 and a second segment member 1120 of a measurement device according to an example embodiment of the present disclosure may form a first angle θ1.

Referring to FIG. 14B, as a case in which the body shape or the measurement part is thick compared to that of FIG. 14A, it can be seen that a second angle θ2 formed by the first segment member 1110 and the second segment member 1120 of the measurement device according to an example embodiment of the present disclosure is increased compared to the first angle θ1.

The rotational coupling part 1050 coupled to the sample part 1100 may further include an angle sensor.

An angle value between respective segment members that rotate may be measured by the angle sensor included in the rotational coupling part 1050, and a circumference, length or size of the measurement part may be identified through this angle value. In addition, a body shape of an examinee, a shape of the measurement part, or the like may be identified.

Figure 15A:
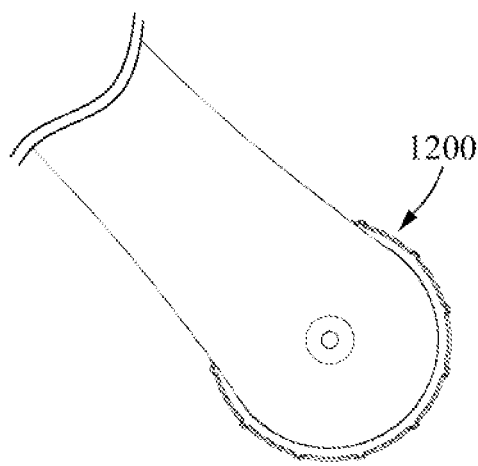
FIGS. 15A and 15B are schematic diagrams illustrating a length measurement part of a bioimpedance measurement device according to the present disclosure.
Figure 15B:
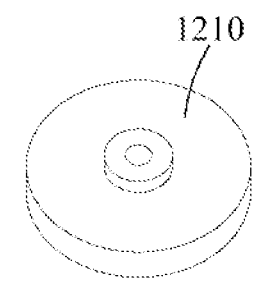
Figure 15B:
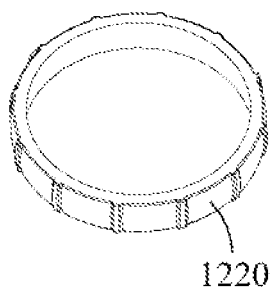

FIGS. 15A and 15B are schematic diagrams illustrating a length measurement part of a bioimpedance measurement device according to the present disclosure.

Figure 16:
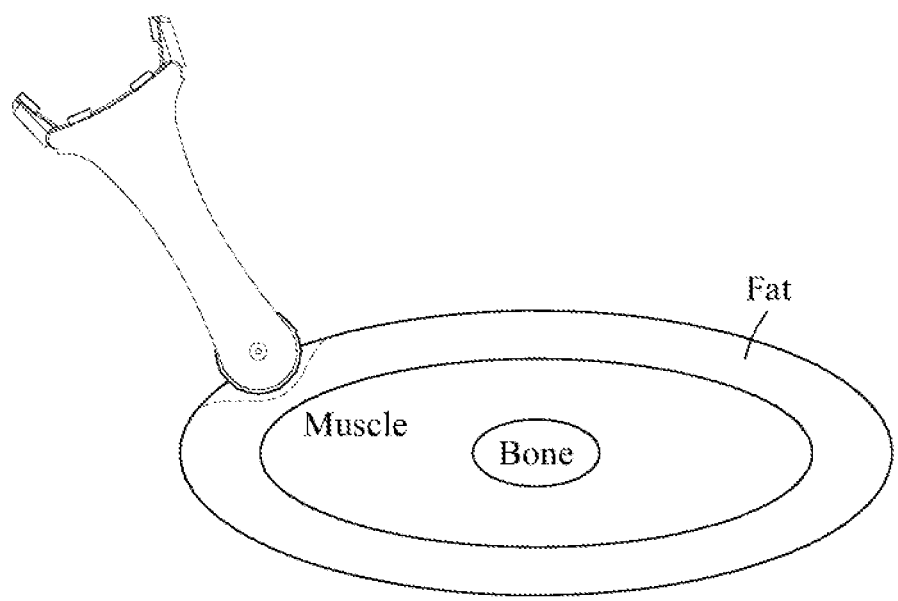
FIG. 16 is a schematic diagram illustrating a state in which a circumference is measured by a bioimpedance measurement device according to the present disclosure.

FIG. 16 is a schematic diagram illustrating a state in which a circumference is measured by a bioimpedance measurement device according to the present disclosure.

Referring to FIG. 15A, a length measurement part 1200 may serve to measure a circumference or length of an examinee. The length measurement part 1200 may be rotatably coupled to another side of the body 1000. The length measurement part 1200 may rotate about a rotational shaft penetrating through the other side of the body 1000. At this time, the rotational shaft may penetrate through the other side of the body 1000 vertically or horizontally, but a penetration direction is not limited thereto, and the rotational shaft may penetrate through the other side of the body 1000 in any direction, and the length measurement part 1200 may rotate about this rotational shaft.

Referring to FIG. 15B, the length measurement part 1200 may include a central part 1210 and an outer part 1220.

The central part 1210 may have a hollow disk shape, but is not limited thereto and may have any shape, for example, a square plate, a hexagonal plate, or the like. A material of the central part 1210 may be made of PC ABS, POM, or the like, but is not limited thereto, and any known material is possible.

The outer part 1220 may have a protrusion part formed on an outer surface thereof. The outer part 1220 may have a donut shape, and may be fittingly coupled to the central part 1210. The outer part 1220 may come into direct contact with the examinee so as to measure a circumference or length of the measurement part. A material of the outer part 1220 may be made of silicon, but it is not limited thereto, and any known material is possible as long as it provides sufficient frictional force with the examinee so that the length measurement part 1200 does not slide on a surface of the examinee.

The length measurement part 1200 may perform a rolling operation on a part of the surface of the examinee. The length measurement part 1200 may include an encoder therein to measure a circumference or length of the examinee based on the measured number of rotations. For example, when the length measurement part 1200 performs a rolling operation to correspond to a circumference or length of ½ of the measurement part, twice a circumference or length value calculated based on the number of rotations of the length measurement part 1200 may be a total circumference or length of the measurement part. However, referring to FIG. 16, in case that the examinee is not a rigid body when the circumference or length of the examinee is measured by the length measurement part 1200, the examinee may be pressed by elasticity of the examinee, and thus, an exact circumference or length may not be calculated by simply applying twice. Therefore, the total circumference or length of the examinee may be more accurately calculated by multiplying an appropriate correlation coefficient obtained through an experiment depending on the total circumference or length, the elasticity of the examinee based on an amount of fat, and the like.

Figure 17:
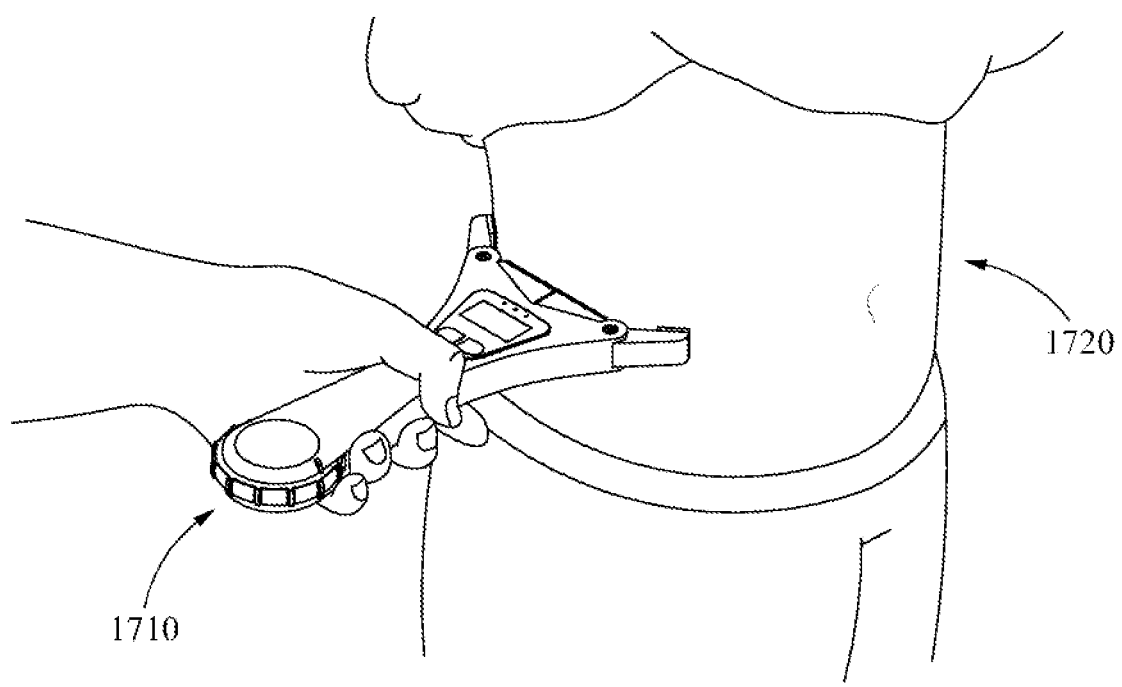
FIG. 17 is a diagram illustrating a process of measuring a bioimpedance according to an example embodiment.

FIG. 17 is a diagram illustrating a process of measuring a bioimpedance according to an example embodiment.

Referring to FIG. 17, an example in which a bioimpedance measurement device 1710 measures a bioimpedance of a subject to be measured 1720 is illustrated. According to an example embodiment, the bioimpedance measurement device 1710 may measure the bioimpedance of the subject to be measured 1720 by coming into contact with a side part of the subject to be measured 1720. At this time, a guide message instructing the subject to be measured 1720 to take a posture with arms crossed in a state in which a top is half removed so that an abdomen of the subject to be measured 1720 is completely visible may be provided to the subject to be measured 1720. In addition, a guide message may be provided so that the bioimpedance measurement device 1710 comes into contact with a side of the subject to be measured 1720, which is a part directly in contact with the bioimpedance measurement device 1710, after the side is wetted with an electrolyte tissue or a wet tissue. In addition, a guide message instructing to forcefully push all electrodes of the bioimpedance measurement device 1710 to come into close contact with a measurement part, and to bring the bioimpedance measurement device 1710 into contact with the subject to be measured 1720 in a manner of pressing down the bioimpedance measurement device 1710 diagonally when contact is not properly made depending on a body shape of the subject to be measured 1720 may be provided.

FIGS. 18A to 18D are diagrams illustrating a screen for guiding a pressure applied when measuring a bioimpedance according to an example embodiment.

Referring to FIGS. 18A to 18D, examples of screens displayed on a display provided in a bioimpedance measurement device according to an example embodiment are illustrated. These screens may be displayed based on an output of a pressure sensor provided in the bioimpedance measurement device. In an impedance measurement mode, when the bioimpedance measurement device comes into close contact with a subject to be measured, whether contact is made may be automatically sensed, so that impedance measurement may be started without an additional button operation. Here, the bioimpedance measurement device may be the bioimpedance measurement device of FIG. 1A or the bioimpedance measurement device of FIG. 9.

According to an example embodiment, in order to accurately measure the bioimpedance of the subject to be measured, the bioimpedance measurement device may need to come into close contact with the subject to be measured with an appropriate level of pressure. Here, the appropriate level of pressure may have a predetermined range, and when a pressure measured by the pressure sensor falls within the range, the bioimpedance measurement device may recognize that the appropriate level of pressure is applied, and may complete bioimpedance measurement.

Figure 18A:
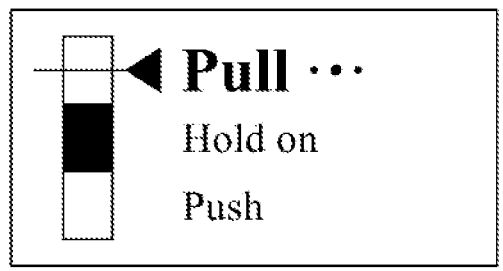
FIGS. 18A to 18D are diagrams illustrating a screen for guiding a pressure applied when measuring a bioimpedance according to an example embodiment.

FIG. 18A illustrates a screen displayed when the pressure applied to the bioimpedance measurement device by close contact with a subject to be measured is too high. For example, when the pressure measured by the pressure sensor is higher than an upper limit of the predetermined range, the screen may be displayed.

Figure 18B:
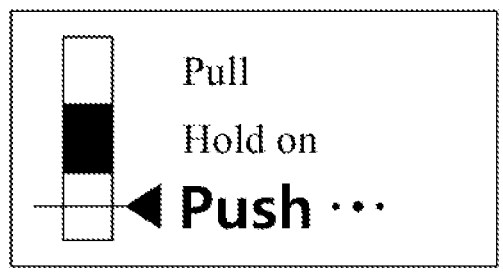

FIG. 18B illustrates a screen displayed when the pressure applied to the bioimpedance measurement device by close contact with the subject to be measured is too low. For example, when the pressure measured by the pressure sensor is lower than a lower limit of the predetermined range, the screen may be displayed.

Figure 18C:
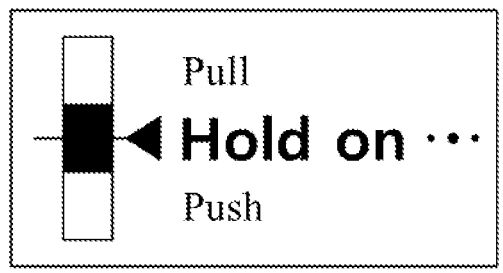

FIG. 18C illustrates a screen displayed when the pressure applied to the bioimpedance measurement device by close contact with the subject to be measured is at an appropriate level. For example, when the pressure measured by the pressure sensor falls within the predetermined range, the screen may be displayed. Depending on the example embodiment, feedback informing that a bioimpedance is being measured because an appropriate level of pressure is applied may be provided to the subject to be measured or an examiner that examines the subject to be measured. For example, a green LED may be turned on, and a measurement beep may be outputted at a predetermined time interval (for example, 1 second and the like). Conversely, when the bioimpedance is not measured because the applied pressure does not fall within the predetermined range, a blue LED may be turned on, and an additional measurement beep may not be outputted.

As such, it is possible to identify whether first to fourth electrodes come into close contact with the subject to be measured with an appropriate level of pressure using the pressure sensor. Furthermore, feedback depending on whether a pressure applied to one or more electrodes of the first to fourth electrodes by close contact with the subject to be measured satisfies a predetermined condition may be determined based on an output of the pressure sensor, and may be provided to the subject to be measured. As a result, it is possible to effectively induce the electrodes to come into close contact with the subject to be measured with the appropriate level of pressure. For example, the feedback may be displayed in the form of a gauge, as illustrated in FIGS. 18A to 18C.

According to an example embodiment, a certain amount of time (for example, 0.5 seconds) may be required to measure the bioimpedance. Therefore, it may be required to maintain a constant posture for stable bioimpedance measurement. For example, when a change amount of a measured bioimpedance value is within 0.3 ohms and a change amount of a measured pressure gauge is within 2 points, a measurement stabilization condition may be determined to be satisfied, and bioimpedance measurement may be completed. When the measurement stabilization condition is not satisfied within a predetermined time (for example, 15 seconds and the like), a message for inducing re-measurement may be outputted.

Figure 18D:
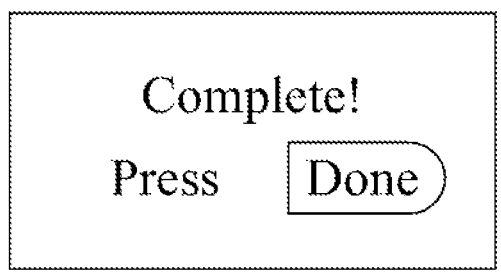
Figure 18D:
Figure 18D:
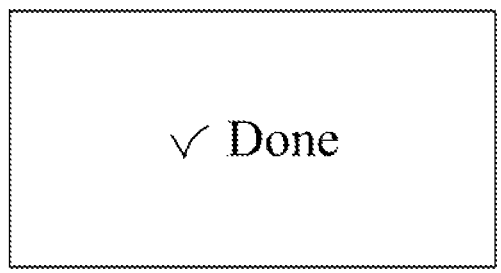

FIG. 18D illustrates screens on which bioimpedance measurement is completed because the measurement stabilization condition is satisfied. At this time, a sound effect indicating that measurement is completed (for example, "beep", and the like) may be outputted together. Thereafter, the bioimpedance measurement device may be switched to be in a waist circumference measurement mode, which will be described with reference to FIGS. 19A to 19D.

FIGS. 19A to 19D are diagrams illustrating a process of measuring a circumference or length of a subject to be measured according to an example embodiment.

Figure 19A:
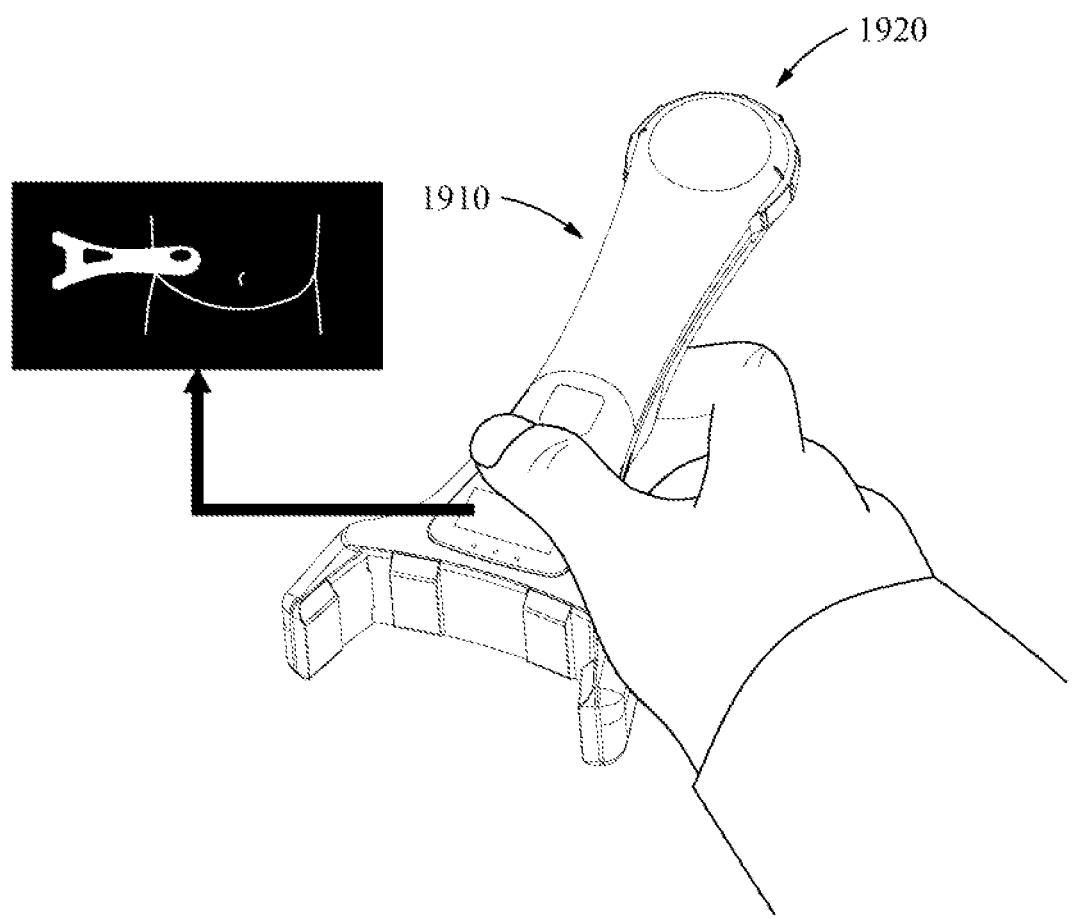
FIGS. 19A to 19D are diagrams illustrating a process of measuring a circumference or length of a subject to be measured according to an example embodiment.

Referring to FIG. 19A, an example of gripping a bioimpedance measurement device 1910 so as to measure a circumference or length of a subject to be measured according to an example embodiment is illustrated. Electrodes for bioimpedance measurement may be positioned at one end of the bioimpedance measurement device 1910, and a length measurement part 1920 for circumference or length measurement may be positioned at another end of the bioimpedance measurement device 1910. When the circumference or length is measured, a screen instructing a circumference/length measurement mode may be displayed on a display of the bioimpedance measurement device 1910.

Figure 19B:
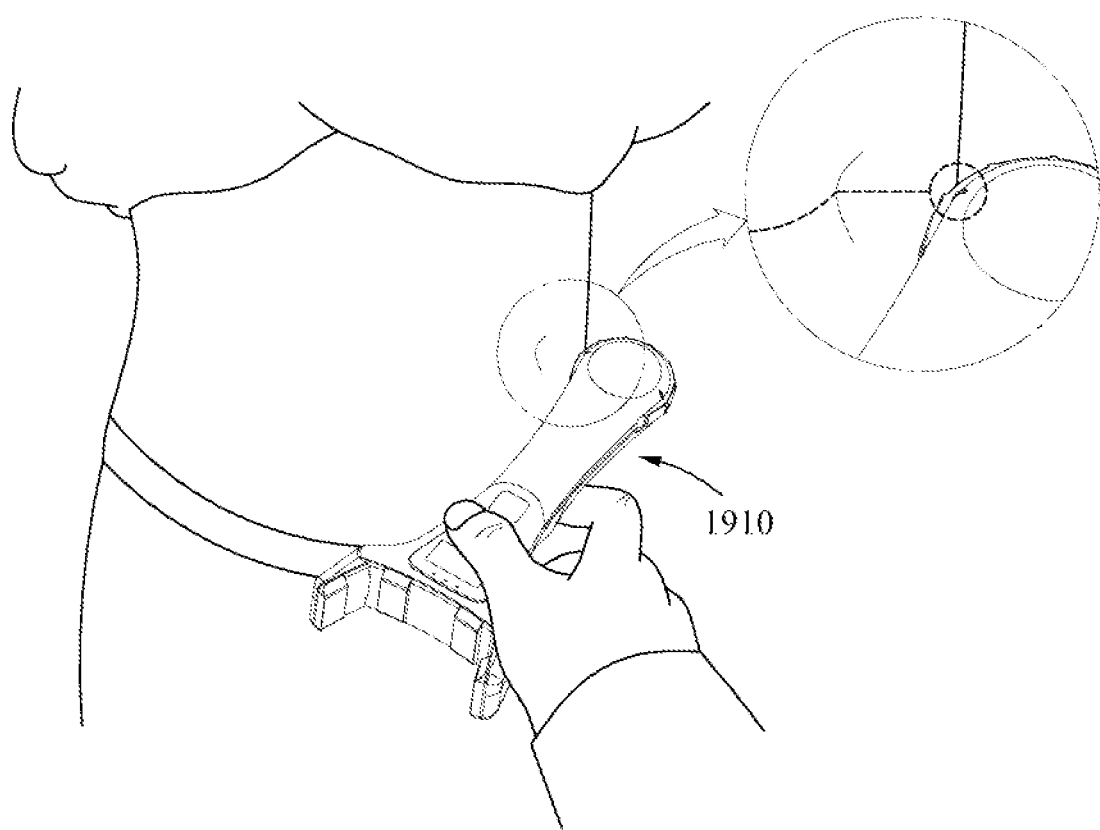
Figure 19C:
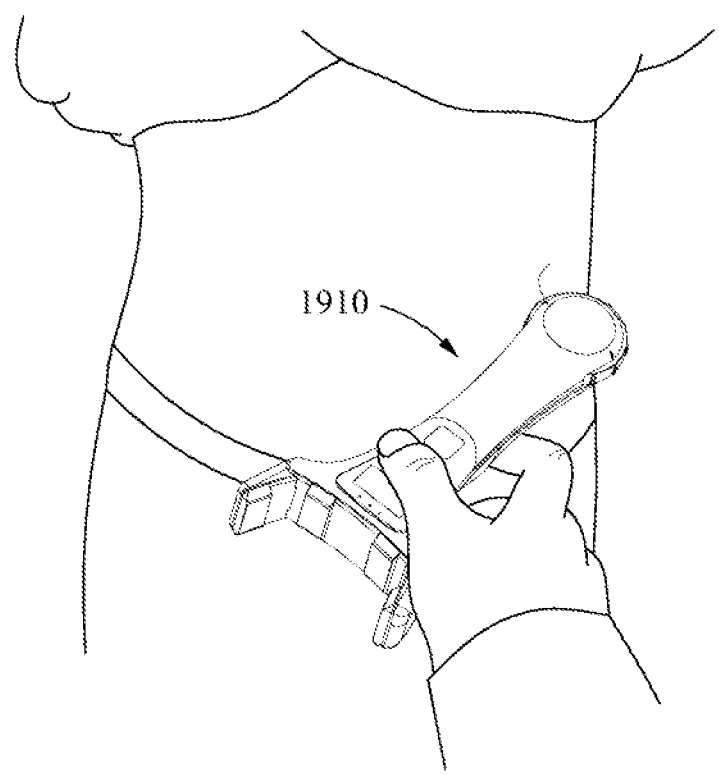

Referring to FIGS. 19B and 19C, an example for explaining a start of waist circumference measurement of a subject to be measured according to an example embodiment is illustrated. For example, waist circumference measurement may be performed based on a right half body of the subject to be measured. A length measurement part may have a wheel start point that is a start reference, and measurement may be started after the wheel start point is aligned with a navel of the subject to be measured. As the bioimpedance measurement device 1910 moves from the navel to a spine part of a back of the subject to be measured, the circumference may be measured while a wheel continues to rotate, and at this time, the wheel may need to be maintained in a state of being horizontal at a height of the navel.

When the length measurement part rotates in close contact with the subject to be measured to measure the circumference or length of the subject to be measured, feedback as to whether circumference or length measurement is normally performed may be provided. For example, detent feedback may be provided when the wheel of the length measurement part rotates. Here, the detent feedback refers to feedback of a tactile feeling whenever the wheel rotates at a predetermined angle, and for example, may indicate that a feeling of being stuck with a snap is generated whenever the wheel rotates at the predetermined angle.

Alternatively, when the length measurement part rotates in close contact with the subject to be measured to measure the circumference or length of the subject to be measured, feedback based on at least one of a rotational speed and a rotational direction of the length measurement part may be provided. For example, a predetermined sound effect (for example, a beep sound) may be generated at a time interval depending on a wheel rotational speed of the length measurement part. As the rotational speed increases, the beep sound may be generated at a short time interval, and as the rotational speed decreases, the beep sound may be generated at a long time interval. In addition, when the circumference or length is measured, the wheel may need to rotate in one direction. However, when the wheel rotates in another direction, the beep sound informing that the rotational direction is incorrect may be generated. In addition, with respect to rotation of the wheel in an opposite direction, the measured circumference or length of the subject to be measured may be corrected.

Through the feedback on rotation, the subject to be measured and/or the examiner who performs circumference measurement may be intuitively aware of whether measurement is being performed normally because the wheel is currently rotating appropriately.

Figure 19D:
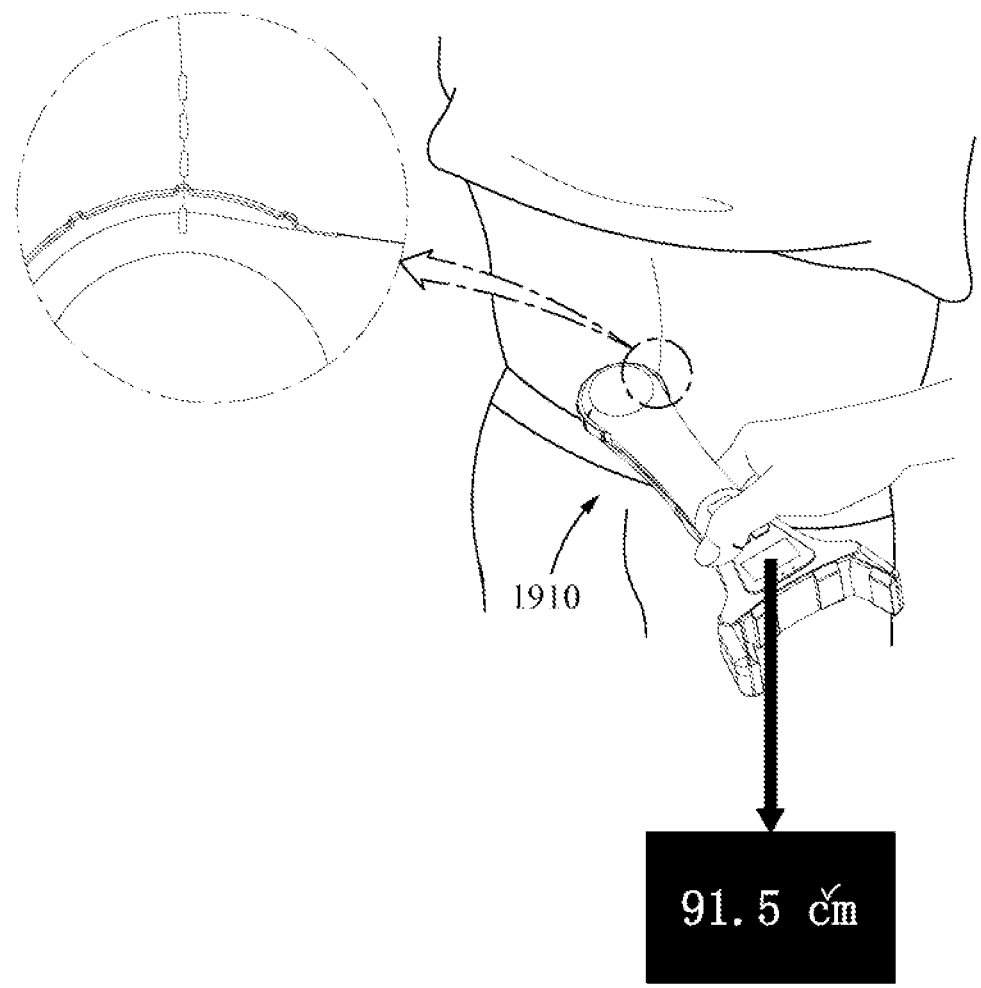

Referring to FIG. 19D, an example for explaining an end of waist circumference measurement of a subject to be measured according to an example embodiment is illustrated. For example, a length measurement part of the bioimpedance measurement device 1910 may have an wheel end point that is an end reference, and measurement may be terminated while the wheel end point is aligned with a spine part of the subject to be measured. The bioimpedance measurement device 1910 may convert a right half body circumference of the subject to be measured that is measured by rotation of the wheel into a total circumference (for example, a half body circumference×2), and may display a result thereof on a display of the bioimpedance measurement device 1910. At this time, the wheel start point and the wheel end point may be implemented as different points (for example, a 180-degree difference on the wheel) or the same point.

As such, the bioimpedance measurement device 1910 may measure a partial circumference of the subject to be measured and convert the partial circumference to a total circumference, thereby easily and efficiently performing circumference measurement on the subject to be measured. In addition, other example embodiments of measuring the partial circumference of the subject to be measured (for example, measuring ⅓, ¼, or the like of the total circumference) may be applied without limitation.

FIGS. 20A to 20D are diagrams illustrating an operation mode of a bioimpedance measurement device according to an example embodiment.

Figure 20A:
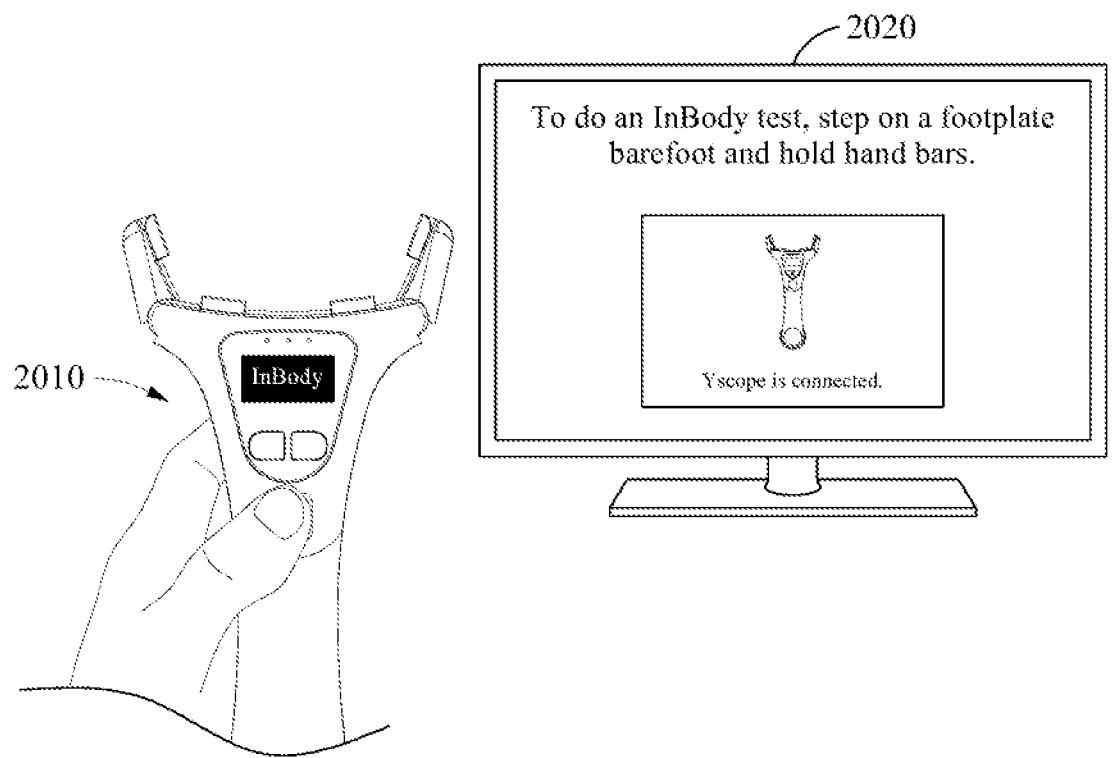
FIGS. 20A to 20D are diagrams illustrating an operation mode of a bioimpedance measurement device according to an example embodiment.
Figure 20B:
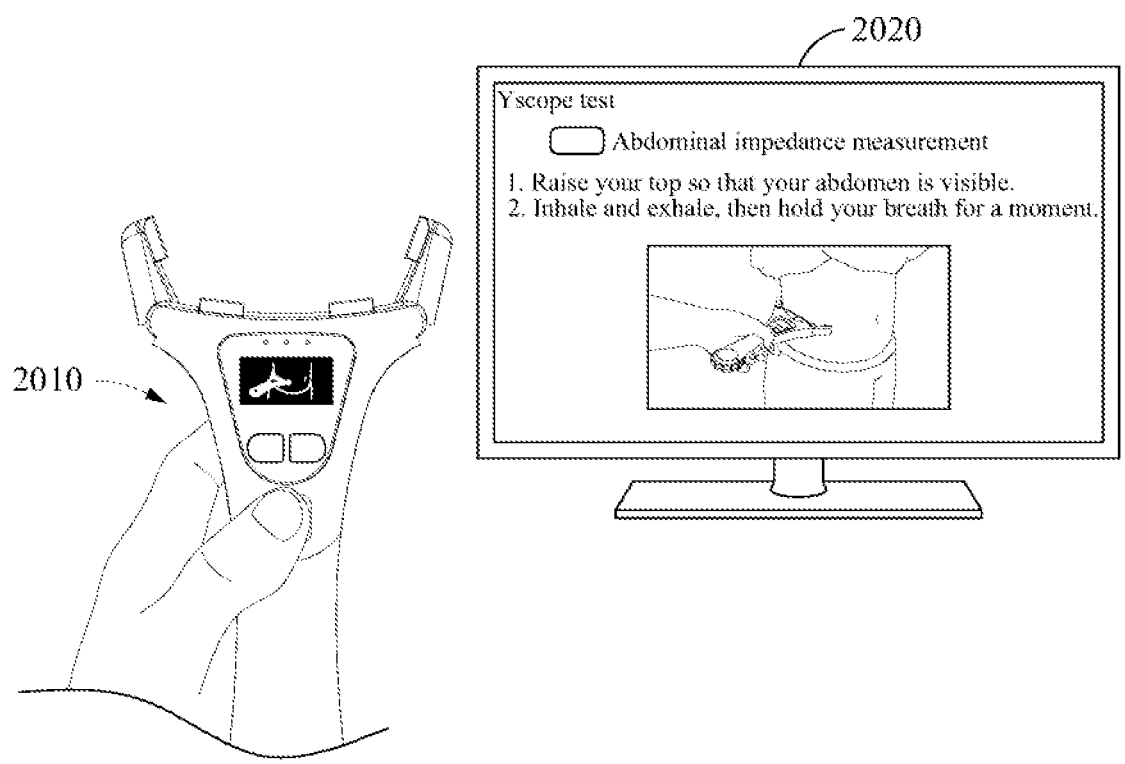
Figure 20C:
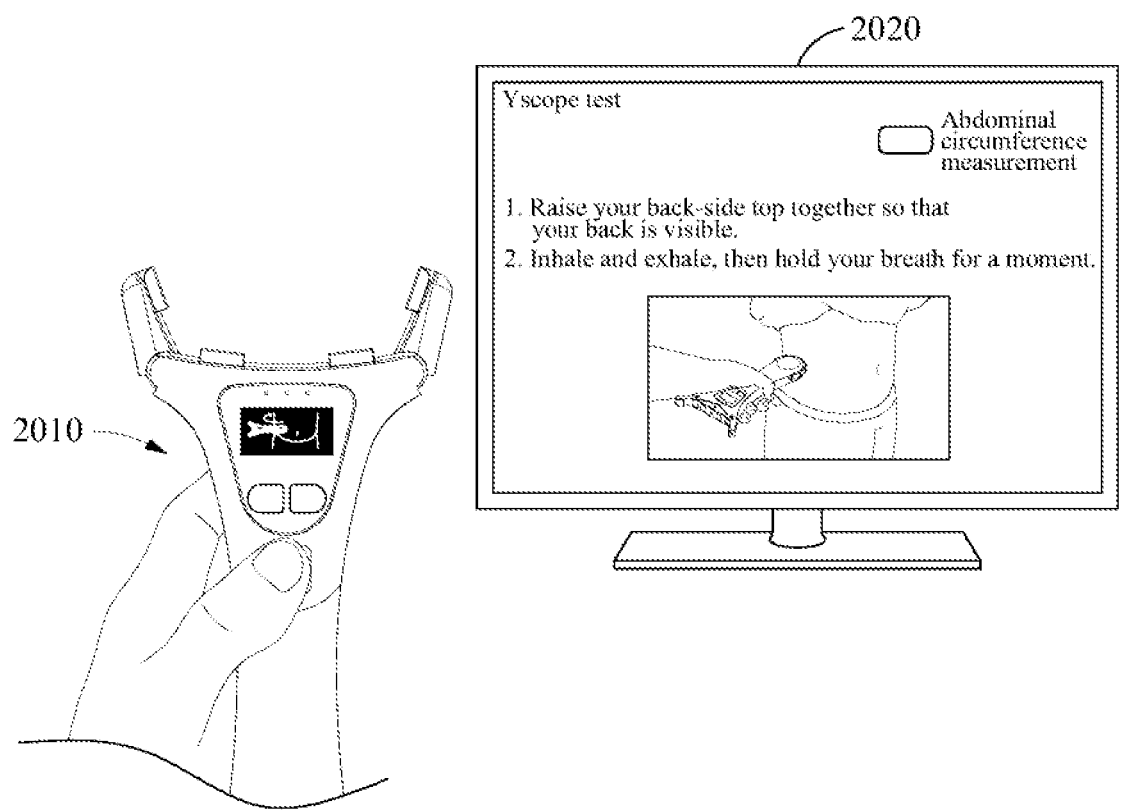

Referring to FIGS. 20A to 20C, examples of interworking between a bioimpedance measurement device 2010 and a display device 2020 according to an example embodiment are illustrated. The display device 2020 according to an example embodiment, which is an additional device distinguished from the bioimpedance measurement device 2010, may display a screen depending on an operation mode of the bioimpedance measurement device 2010, and may also display a result measured by the bioimpedance measurement device 2010. FIG. 20A illustrates a state in which the bioimpedance measurement device 2010 and the display device 2020 are connected to each other. FIG. 20B illustrates an abdominal impedance measurement mode, and FIG. 20C illustrates an abdominal circumference measurement mode.

When no operation is performed for more than a predetermined time (for example, 5 minutes, and the like) in a state in which a measurement screen is displayed, the bioimpedance measurement device 2010 may be turned off to prevent battery consumption.

Figure 20D:
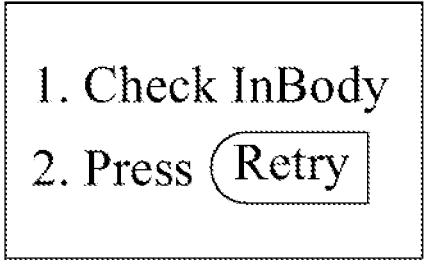

Referring to FIG. 20D, when a subject to be measured or an examiner determines that a result measured in impedance measurement and the circumference measurement are abnormal, re-measurement is possible through a Retry button provided in the bioimpedance measurement device 2010, and a new measurement value may be updated through a mode change after a measurement result is confirmed.

The above-described example embodiments may be applied to both the bioimpedance measurement device of FIG. 1A and the bioimpedance measurement device of FIG. 9 by those skilled in the art, unless the example embodiments are explicitly restricted or under special circumstances in which a normal operation cannot be expected.

Figure 21:
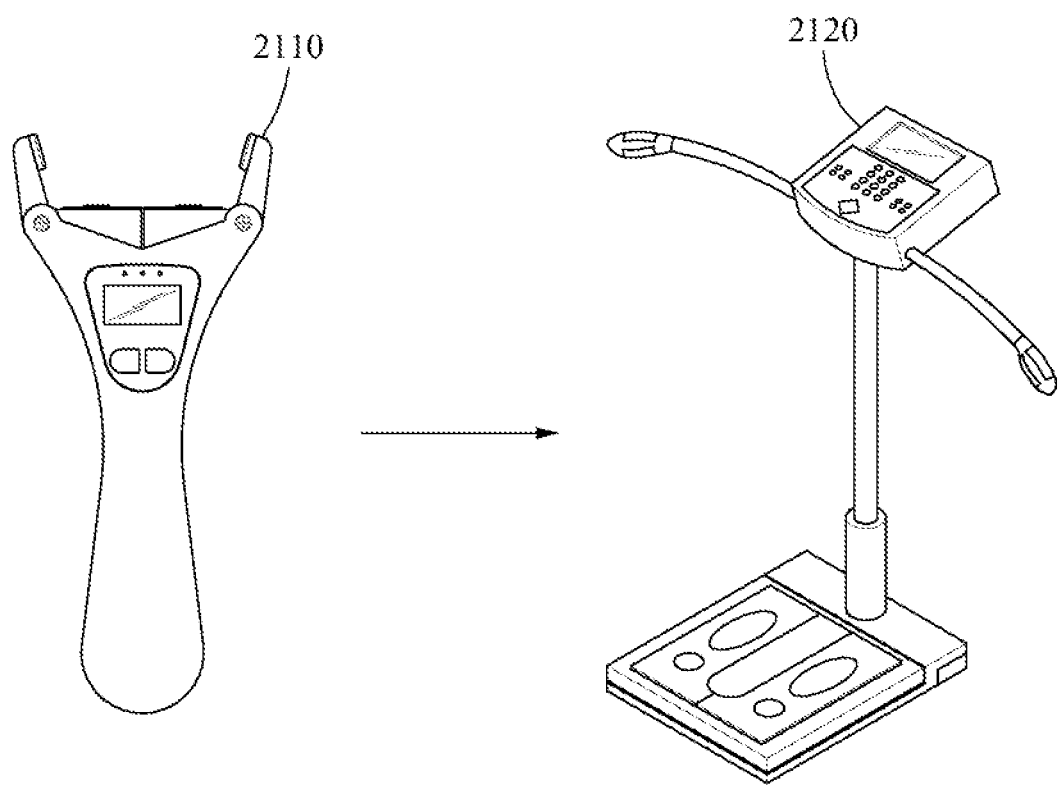
FIGS. 21 and 22 are diagrams illustrating an example embodiment of linkage of a bioimpedance measurement device according to an example embodiment.
Figure 22:
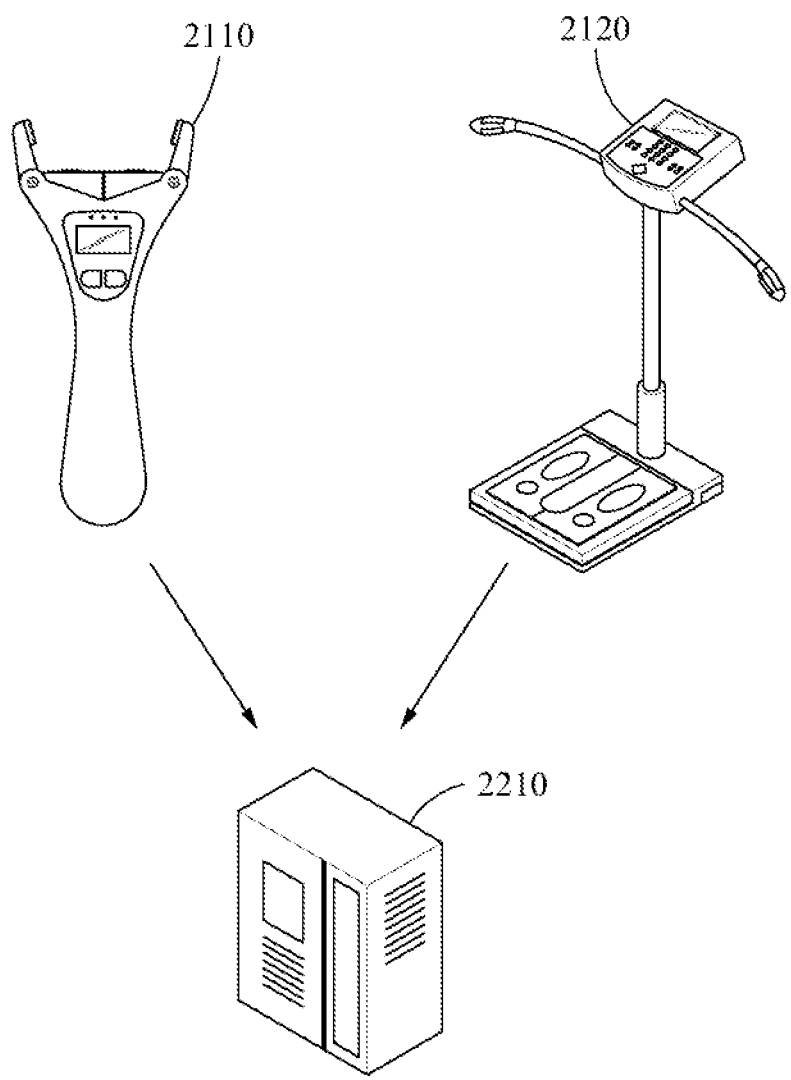

FIGS. 21 and 22 are diagrams illustrating an example embodiment of linkage of a bioimpedance measurement device according to an example embodiment.

Referring to FIG. 21, an example for explaining linkage of a bioimpedance measurement device 2110 and an external device 2120 according to an example embodiment is illustrated.

The bioimpedance measurement device 2110 is a device for measuring a bioimpedance of a subject to be measured using first to fourth electrodes, and thus the foregoing descriptions may be applied thereto. In addition, depending on the example embodiment, while the subject to be measured approaches and comes into contact, the bioimpedance measurement device 2110 may estimate a circumference of the subject to be measured using at least one of a degree to which the second electrode rotates toward the grip, a degree to which the fourth electrode rotates toward the grip, a degree to which the first electrode is spread or gathered, and a degree to which the third electrode is spread or gathered, or may measure the circumference of the subject to be measured through a length measurement part positioned at another side of a body part.

The external device 2120 may be connected to the bioimpedance measurement device 2110 through a wireless network and/or a wired network. For example, the bioimpedance measurement device 2110 and the external device 2120 may perform communication with each other through Bluetooth, Wi-Fi, or the like. The external device 2120 may receive at least one of the bioimpedance and the circumference of the subject to be measured from the bioimpedance measurement device 2110.

In addition, the external device 2120 may measure a weight of the subject to be measured as the subject to be measured steps on a footplate. The external device 2120 may include a plurality of electrodes, and may measure a whole-body impedance or body part-specific impedance of the subject to be measured through the electrodes. For example, the plurality of electrodes of the external device 2120 may respectively come into contact with both feet and both hands of the subject to be measured, so that the whole-body impedance or body part-specific impedance of the subject to be measured may be measured.

In addition, the external device 2120 may receive body information of the subject to be measured from the subject to be measured. For example, the body information may include a height, age, gender, and the like of the subject to be measured.

The external device 2120 may determine a body composition of the subject to be measured based on at least one of data received from the bioimpedance measurement device 2110 (for example, the bioimpedance and/or circumference of the subject to be measured), the weight and the whole-body impedance or body part-specific impedance of the subject to be measured that are measured by the external device, and the body information of the subject to be measured inputted into the external device. The bioimpedance and circumference of the subject to be measured that are measured by the bioimpedance measurement device 2110 may be used to measure the body composition of the subject to be measured, thereby effectively improving accuracy in measuring a body composition for an abdomen of the subject to be measured such as visceral fat, abdominal fat, subcutaneous fat, and the like of the subject to be measured.

The external device 2120 may provide, to the subject to be measured, the body composition of the subject to be measured. For example, a body composition measurement result of the subject to be measured may be displayed on a display of the external device 2120, may be outputted in the form of a result sheet by the external device 2120 or an additional device connected to the external device 2120, may be transmitted from the external device 2120 to the bioimpedance measurement device 2110 and displayed on a display of the bioimpedance measurement device 2110, or may be transmitted to a portable terminal (for example, smart phone, tablet, and the like) possessed by the subject to be measured and displayed on the portable terminal. In addition, the body composition measurement result may be provided to the subject to be measured in various forms.

Referring to FIG. 22, an example for explaining linkage of the bioimpedance measurement device 2110, the external device 2120, and a server 2210 according to an example embodiment is illustrated.

The bioimpedance measurement device 2110 is a device for measuring a bioimpedance of a subject to be measured using first to fourth electrodes, and thus the foregoing descriptions may be applied thereto. In addition, depending on the example embodiment, while the subject to be measured approaches and comes into contact, the bioimpedance measurement device 2110 may estimate a circumference of the subject to be measured using at least one of a degree to which the second electrode rotates toward the grip, a degree to which the fourth electrode rotates toward the grip, a degree to which the first electrode is spread or gathered, and a degree to which the third electrode is spread or gathered, or may measure the circumference of the subject to be measured through a length measurement part positioned at another side of a body part.

In addition, the external device 2120 may measure a weight of the subject to be measured as the subject to be measured steps on a footplate. The external device 2120 may include a plurality of electrodes, and may measure a whole-body impedance or body part-specific impedance of the subject to be measured through the electrodes. For example, the plurality of electrodes of the external device 2120 may respectively come into contact with both feet and both hands of the subject to be measured, so that the whole-body impedance or body part-specific impedance of the subject to be measured may be measured. In addition, the external device 2120 may receive body information of the subject to be measured from the subject to be measured. For example, the body information may include a height, age, gender, and the like of the subject to be measured.

The bioimpedance measurement device 2110 and the external device 2120 may be connected to the server 2210 through a wireless network and/or a wired network. For example, the bioimpedance measurement device 2110 and the external device 2120 may perform communication with the server 2210 through Bluetooth, Wi-Fi, or the like. The server 2210 may receive at least one of the bioimpedance and circumference of the subject to be measured from the bioimpedance measurement device 2110. In addition, the server 2210 may receive, from the external device 2120, the weight and the whole-body impedance or body part-specific impedance of the subject to be measured that are measured by the external device 2120, and the body information of the subject to be measured inputted into the external device.

According to another example embodiment, the bioimpedance measurement device 2110 may transmit, to the external device 2120, at least one of a bioimpedance and a circumference of a subject to be measured, and the external device 2120 may transmit, to the server 2210, at least one of the bioimpedance and the circumference of the subject to be measured together with a weight, a whole-body impedance or body part-specific impedance, and body information of the subject to be measured.

The server 2210 may determine a body composition of the subject to be measured based on at least one of the bioimpedance and circumference of the subject to be measured that are measured by the bioimpedance measurement device 2110, the weight and the whole-body impedance or body part-specific impedance of the subject to be measured that are measured by the external device 2120, and the body information of the subject to be measured that is inputted into the external device 2120.

At this time, the server 2210 may determine the body composition of the subject to be measured further using biometric data stored in the server 2210. The biometric data stored in the server 2210 may include a measurement result performed by the subject to be measured in the past and a body composition determination result corresponding thereto, and may further include a measurement result of another user and a body composition determination result corresponding thereto. As such, by using the biometric data stored/managed in the server 2210, the body composition of the subject to be measured may be more accurately determined. Depending on the example embodiment, a change in the body composition of the subject to be measured as well as a current body composition determination result may be provided in chronological order, or comparative data showing a top percentage to which the current body composition determination result belongs by comparing the current body composition determination result to those of other users may be also provided.

The server 2210 may provide, to the subject to be measured, the body composition measurement result of the subject to be measured. For example, the body composition measurement result of the subject to be measured may be transmitted from the server 2210 to the external device 2120 and displayed on a display of the external device 2120, may be outputted in the form of a result sheet by the external device 2120 or an additional device connected to the external device 2120, may be transmitted from the server 2210 to the bioimpedance measurement device 2110 and displayed on a display of the bioimpedance measurement device 2110, or may be transmitted from the server 2210 to a portable terminal (for example, smart phone, tablet, and the like) possessed by the subject to be measured and displayed on the portable terminal. In addition, the body composition measurement result may be provided to the subject to be measured in various forms.

The above-described example embodiments may be implemented using a hardware component, a software component and/or a combination thereof. A processing device may be implemented using one or more general-purpose or special purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an OS and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described hardware devices may be configured to act as one or more software modules in order to perform the operations of the above-described example embodiments, or vice versa.

The components described in the example embodiments may be implemented by hardware components including, for example, at least one digital signal processor (DSP), a processor, a controller, an application-specific integrated circuit (ASIC), a programmable logic element, such as a field programmable gate array (FPGA), other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

The invention claimed is:

1. A bioimpedance measurement device, the device comprising:
a body part configured to accommodate a measurement circuit, the body part including a grip that can be gripped by a hand;
a first electrode and a second electrode coupled to a first shaft provided on one side of the body part, the first electrode and the second electrode configured to rotate about the first shaft; and
a third electrode and a fourth electrode coupled to a second shaft provided on the one side of the body part at a position different from that of the first shaft, the third electrode and the fourth electrode configured to rotate about the second shaft,
wherein the device is configured to measure a bioimpedance of a subject to be measured when the subject to be measured approaches, and is surrounded by and comes into contact with the first electrode, the second electrode, the third electrode, and the fourth electrode, and
wherein the measurement circuit is configured to determine that the bioimpedance measurement result is not valid when at least one of the second electrode and the fourth electrode rotates to a limit toward the grip and is pressed, while being pressed by the subject to be measured.

2. The device of claim 1, wherein the second electrode is configured to accommodate the subject to be measured deeper than when the subject to be measured begins to come into contact with the second electrode, by being pressed by the subject to be measured and rotating toward the grip.

3. The device of claim 2, wherein the second electrode is supported by an elastic body so as to be restored back to a position before rotation when the subject to be measured is spaced apart from the second electrode.

4. The device of claim 2, wherein the fourth electrode is adjacent to the second electrode, and is configured to accommodate the subject to be measured deeper than when the subject to be measured begins to come into contact with the fourth electrode, by being pressed by the subject to be measured and rotating toward the grip.

5. The device of claim 4, wherein a degree to which the fourth electrode rotates toward the grip may be different from a degree to which the second electrode rotates toward the grip.

6. The device of claim 1, wherein the measurement circuit is configured to estimate a part of the subject to be measured that is in contact by comparing a degree to which the second electrode rotates toward the grip and a degree to which the fourth electrode rotates toward the grip, while being pressed by the subject to be measured.

7. The device of claim 1, wherein the measurement circuit is configured to estimate a part of the subject to be measured that is in contact by comparing a degree to which the first electrode is spread and a degree to which the third electrode is spread, while being pressed by the subject to be measured.

8. The device of claim 1, wherein the first electrode and the third electrode are spread or gathered depending on a circumference of the subject to be measured that approaches and comes into contact.

9. The device of claim 1, wherein the measurement circuit is configured to estimate a circumference of the subject to be measured using at least one of a degree to which the second electrode rotates toward the grip, a degree to which the fourth electrode rotates toward the grip, a degree to which the first electrode is spread or gathered, and a degree to which the third electrode is spread or gathered, while the subject to be measured approaches and comes into contact.

10. The device of claim 1, further comprising:
a pressure sensor configured to measure a pressure when the subject to be measured approaches, and is surrounded by and comes into contact with the first electrode, the second electrode, the third electrode, and the fourth electrode,
wherein the bioimpedance of the subject to be measured is measured when the pressure measured by the pressure sensor falls within a predetermined range.

11. The device of claim 10, wherein
the body part includes a first part including the first to fourth electrodes and a second part including the grip that can be gripped by the hand, and
the pressure sensor is disposed between the first part and the second part, and is configured to measure a pressure applied by the first part to the second part when the subject to be measured approaches, and is surrounded by and comes into close contact with the first electrode, the second electrode, the third electrode, and the fourth electrode.

12. The device of claim 1, further comprising:
a communicator configured to transmit, to an external device, the bioimpedance and a circumference of the subject to be measured,
wherein a body composition of the subject to be measured is determined based on at least one of the bioimpedance and the circumference of the subject to be measured, a weight and a whole-body impedance or body part-specific impedance of the subject to be measured that are measured by the external device, and body information of the subject to be measured that is inputted into the external device.

13. The device of claim 1, further comprising:
a communicator configured to transmit, to a server, the bioimpedance and a circumference of the subject to be measured,
wherein a body composition of the subject to be measured is determined based on at least one of the bioimpedance and the circumference of the subject to be measured, a weight and a whole-body impedance or body part-specific impedance of the subject to be measured that are measured by an external device that performs communication with the bioimpedance measurement device, body information of the subject to be measured that is inputted into the external device, and biometric data stored in the server.

14. An operation method of a bioimpedance measurement device, the operation method comprising:
sensing a movement of at least one of a first electrode, a second electrode, a third electrode, and a fourth electrode provided in the bioimpedance measurement device when a subject to be measured approaches the bioimpedance measurement device, and is surrounded by and comes into contact with the bioimpedance measurement device; and
measuring a bioimpedance of the subject to be measured using at least one of the first electrode, the second electrode, the third electrode, and the fourth electrode,
wherein the first electrode and the second electrode are coupled to a first shaft provided on one side of the bioimpedance measurement device to rotate about the first shaft, and
the third electrode and the fourth electrode are coupled to a second shaft on the one side of the bioimpedance measurement device at a position different from that of the first shaft to rotate about the second shaft, and wherein the measurement circuit is configured to determine that the bioimpedance measurement result is not valid when at least one of the second electrode and the fourth electrode rotates to a limit toward a grip and is pressed, while being pressed by the subject to be measured.

15. A bioimpedance measurement device, the device comprising:
a body part configured to accommodate a measurement circuit, the body part including a grip that can be gripped by a hand;
a first electrode coupled to a first shaft provided on one side of the body part, the first electrode configured to rotate about the first shaft;
a third electrode coupled to a second shaft provided on the one side of the body part at a position different from that of the first shaft, the third electrode configured to rotate about the second shaft;
a second electrode positioned adjacent to the first electrode between the first electrode and the third electrode; and
a fourth electrode positioned adjacent to the third electrode between the first electrode and the third electrode,
wherein the device is configured to measure a bioimpedance of a subject to be measured when the subject to be measured approaches, and is surrounded by and comes into contact with the first electrode, the second electrode, the third electrode, and the fourth electrode, and
wherein the measurement circuit is configured to determine that the bioimpedance measurement result is not valid when at least one of the second electrode and the fourth electrode rotates to a limit toward the grip and is pressed, while being pressed by the subject to be measured.

16. The device of claim 15, wherein the first electrode and the third electrode are spread in different directions to come into close contact with the subject to be measured as the subject to be measured approaches and comes into contact.

17. The device of claim 15, wherein
the first electrode and the third electrode are coupled to the one side of the body part, and are respectively disposed on a plurality of segment members that are rotatably coupled to each other,
the first to fourth electrodes form a sample part including at least two electrodes for applying a current and at least two electrodes for measuring a voltage, and
an angle between respective segment members is adjusted so that one or more electrodes disposed on the plurality of segment members come into contact with the subject to be measured to correspond to a shape or thickness of the subject to be measured.

18. The device of claim 17, further comprising:
an adjustment mechanism disposed on one side of the body part, the adjustment mechanism configured to adjust rotation of one or more segment members of the sample part,
wherein the sample part is connected to the adjustment mechanism, so that an angle between the plurality of segment members is changed by operation of the adjustment mechanism, and
when an operation state of the adjustment mechanism is released after at least some of the first electrode, the second electrode, the third electrode, and the fourth electrode are brought into contact with a measurement part of the subject to be measured, the angle between the respective segment members is adjusted so that the electrodes disposed on the plurality of segment members come into contact with the subject to be measured to correspond to the shape or thickness of the subject to be measured.

19. The device of claim 15, further comprising:
a length measurement part coupled to another side of the body part, the length measurement part configured to measure a circumference or length of the subject to be measured, and
the length measurement part is configured to rotate about a rotational shaft penetrating through the other side of the body part, and measure the circumference or length of the subject to be measured based on the number of rotations measured by performing a rolling operation on a surface of the subject to be measured.

* * * * *